United States Patent
Tian et al.

(10) Patent No.: US 6,355,807 B1
(45) Date of Patent: Mar. 12, 2002

(54) EFFICIENT SYNTHETIC ROUTES FOR THE PREPARATION OF RHINOVIRUS PROTEASE INHIBITORS AND KEY INTERMEDIATES

(75) Inventors: Qingping Tian; Naresh K. Nayyar; Srinivasan Babu; Junhua Tao; Terence Jarold Moran, all of San Diego; Raymond Dagnino, Jr., El Cajon; Lennert J. Mitchell, Jr., Hemet; Travis Paul Remarchuk, Irvine, all of CA (US); Michael Joseph Melnick, Ann Arbor, MI (US); Steven Lee Bender, Oceanside, CA (US)

(73) Assignee: Agouron Pharmaceuticals, Inc.

( * ) Notice: Subject to any disclaimer, the term of this patent is extended or adjusted under 35 U.S.C. 154(b) by 0 days.

(21) Appl. No.: 09/643,864

(22) Filed: Aug. 23, 2000

Related U.S. Application Data

(60) Provisional application No. 60/150,358, filed on Aug. 24, 1999, and provisional application No. 60/150,365, filed on Aug. 24, 1999.

(51) Int. Cl.$^7$ .................... C07D 207/26; C07D 261/18; C07D 413/12
(52) U.S. Cl. ........................................ 548/248; 548/550
(58) Field of Search ................................. 548/248, 550

(56) References Cited

U.S. PATENT DOCUMENTS

| | | | |
|---|---|---|---|
| 5,166,437 A | 11/1992 | Kairisalo et al. | 564/347 |
| 5,225,585 A | 7/1993 | Schwartz et al. | 558/275 |
| 5,360,927 A | 11/1994 | Chen et al. | 562/459 |
| 5,618,968 A | 4/1997 | Crnic et al. | 560/27 |
| 5,795,750 A | 8/1998 | Kruse et al. | 435/128 |
| 5,847,214 A | 12/1998 | Arosio et al. | 564/347 |
| 5,856,530 A | 1/1999 | Webber et al. | 549/478 |
| 5,962,487 A | * 10/1999 | Webber et al. | 514/378 |
| 6,020,371 A | * 2/2000 | Dragovich et al. | 514/514 |

FOREIGN PATENT DOCUMENTS

| | | |
|---|---|---|
| JP | 62-212329 | 9/1987 |
| WO | WO 97/43305 | 11/1997 |
| WO | WO 98/07420 | 2/1998 |
| WO | WO 98/43950 | 10/1998 |
| WO | WO 99/31122 | 6/1999 |
| WO | WO 99/57135 | 11/1999 |

OTHER PUBLICATIONS

Sebastian Rissom, et al., "Asymmetric Reduction of Acetophenone In Membrane Reactors: Comparison of Oxazaborolidine and Alcohol Dehydrogenase Catalysed Processes" *Tetrahedron: Asymmetry 10*, pp. 923–923 (1999).

Shu–Su Lin, et al. "Continuous Production of L–Alanine with NADH Regeneration by a Nanofiltration Membrane Reactor" *Biosci., Biotech., Biochem.* 61 (12) pp. 2029–2033 (1997).

Stephen Hanessian, et al. "1,3–Asymmetric Induction in Dianionic Allylation Reactions of Amino Acid Derivatives–Synthesis of Functionally Useful Enantiopure Glutamates, Pipecolates and Pyroglutamates" *Tetrahedron Letters 39*, pp. 5887–5890 (1998).

Andrzeg A. Duralski, et al., "Synthesthis of Optically Active Polyunsaturated Diacylglycerols" *Tetrahedron Letters*, vol. 30, No. 27, pp. 3585–3588 (1989).

Keiko Shimamoto, et al. "Synthesis of Four Diastereomeric L–2–(Carboxycyclopropyl) glycines Conformationally Constrained L–Glumate Analogues" *Journal of Organic Chemistry*, vol. 56, pp. 4167–4176 (1991).

Elke Schmidt, et al. "Optimization Of A Process For The Production Of (R)–2–Hydroxyy–4–Phenylbutyric Acid—An Intermediate For Inhibitors Of Angiotensin Converting Enzyme" *Journal of Biotechnology 24*, pp. 315–327 (1992).

Peter S. Dragovich, et al., "Solid–phase Synthesis of Irreversible Human Rhinovirus 3C Protease Inhibitors. Part 1: Optimization of Tripeptides Incorporating N–terminal Amides" *Bioorganic & Medicinal Chemistry 7*, pp. 589–598 (1999).

Peter S. Dragovich, et al., "Structure–Based Design, Synthesis, and Biological Evaluation of Irreversible Human Rhinovirus 3C Protease Inhibitors. 4. Incorporation of $P_1$ Lactam Moieties as 1–Glutamine Replacements" *Journal of Medicinal Chemistry*, vol. 42, No. 7. pp. 1213–1224 (1999).

Peter S. Dragovich, et al., "Structure–Based Design, Synthesis, and Biological Evaluation of Irreversible Human Rhinovirus 3C Protease Inhibitors. 3. Structure–Activity Studies of Ketomethylene–Containing Peptidomimetics" *Journal of Medicinal Chemistry*, vol. 42, No. 7, 1203–1212 (1999).

Hartmuth C. Kolb, et al. "Catalytic Asymmetric Dihydroxylation" *Chemical Reviews*, vol. 94, No. 8, pp.2483–2499 & 2542–2547, (1994).

Marc Larchêveque et al., "A Simple Preparation of R or S Glycidic Esters; Application To The Synthesis of Enantiomerically Pure α–Hydroxyesters" *Tetrahedron Letters*, vol. 28, No. 18, pp. 1993–1996, (1987).

(List continued on next page.)

*Primary Examiner*—Fiona T. Powers

(57) ABSTRACT

Efficient synthetic routes for the preparation of rhinovirus protease inhibitors of formula I, as well as key intermediates useful in those synthetic routes. These compounds of formula I, as well as pharmaceutical compositions that contain these compounds, are suitable for treating patients or hosts infected with one or more picornaviruses (I)

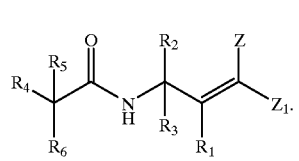

25 Claims, No Drawings

OTHER PUBLICATIONS

Alfred Pollak et al., "Enzyme Immobilization by Condensation Copolymerization into Cross–Linked Polyacrylamide Gels" *Journal of American Chemical Society*, 102, pp.6324–6336 (1980).

Mark D. Bednarski, et al., "Membrane–Enclosed Enzymatic Catalysis (MEEC): A Useful, Practical New Method for the Manipulation of Enzymes in Organic Synthesis" *Journal of American Chemical Society*, 109, pp. 1283–1285 (1987).

Teodozyj Kolasa, "Reactions of α–Hydroxy Carbonyl Compounds with Azodicarboxylates and Triphenylphosphine: Synthesis of α–N–Hydroxy Amino Acid Derivatives" *Journal of Organic Chemistry 52*, pp. 4978–4984 (1987).

Robert V. Hoffman, "An Improved Enantiospecific Synthesis of Statine and Statine Analogs via 4–(N, N–Dibenzylamino)–3–keto Esters" *Journal of Organic Chemistry*, 62. pp. 2292–2297 (1997).

Ethan S. Simon et al., "D–Lactate Dehydrogenase–Substrate Specificity and Use as a Catalyst in the Synthesis of Homochiral 2–Hydroxy Acids" vol. 22, pp. 169–179 (1989).

Franz Effenberger et al., "Enantioselektive Snythese N–substituierter α–Amino–carbonsäuren aus α–Hydroxycarbonsäuren" *Liebigs Ann. Chem.* pp. 314–333 (1986).

Robert V. Hoffman, "A Simple, Stereoselective Synthesis of Ketomethylene Dipeptide Isosteres" *Tetrahedron.* vol. 53, No. 21, pp. 7119–7126 (1997).

Robert V. Hoffman et al., "Synthesis of Cbz–Protected Ketomethylene Dipeptide Isoteres" *Methods in Molecular Medicine*, vol. 23, pp. 103–124.

Karin A. Stein et al., "Enzyme–Catalyzed Regioselective Hydrolysis of Aspartate Diesters" *Journal of Organic Chemistry*, 60, pp. 8110–8112 (1995).

\* cited by examiner

EFFICIENT SYNTHETIC ROUTES FOR THE PREPARATION OF RHINOVIRUS PROTEASE INHIBITORS AND KEY INTERMEDIATES

RELATED APPLICATION DATA

This application relates to U.S. Provisional Patent Application Ser. No. 60/150,358, filed on Aug. 24, 1999.

This application also relates to U.S. Provisional Patent Application Ser. No. 60/150,365, also filed Aug. 24, 1999, entitled "Efficient Methods For The Preparation Of Rhinovirus Protease Inhibitors, Key Intermediates And A Continuous Membrane Reactor Useful For The Preparation Of The Same" having named as inventors: J. Tao, S. Babu, R. Dagnino, Jr., Q. Tian, T. Remarchuk, K. McGee, N. Nayyar, and T. Moran. The aforementioned application also relates to synthetic routes for the preparation of rhinovirus protease inhibitors, as well as key intermediates useful in their preparation. The above-mentioned applications are relied upon and incorporated herein by reference.

TECHNICAL FIELD AND INDUSTRIAL APPLICABILITY OF INVENTION

The present invention relates to an improved process for the preparation of ethyl-3-{(5'-methylisoxazole-3'-carbonyl)-L-ValΨ(COCH$_2$)-L-(4-F-Phe)-L-((S)-Pyrrol-Ala)}-E-propanoate, (also referred to as AG7088), its analogs and of pharmaceutically acceptable salts thereof. The present invention also includes a novel group of key intermediate compounds to be used in the above process.

BACKGROUND OF THE INVENTION

Picornaviruses are a family of tiny non-enveloped positive-stranded RNA-containing viruses that infect humans and other animals. These viruses include the human rhinoviruses, human polioviruses, human coxsackieviruses, human echoviruses, human and bovine enteroviruses, encephalomyocarditis viruses, meningitis viruses, foot and mouth viruses, hepatitis A virus, and others. The human rhinoviruses are a major cause of the common cold.

Proteolytic 3C enzymes are required for the natural maturation of the picornaviruses. Thus, inhibiting the activity of these proteolytic 3C enzymes should represent an important and useful approach for the treatment and cure of viral infections of this nature, including the common cold.

Some small-molecule inhibitors of the enzymatic activity of picornaviral 3C protease (i.e., antipicornaviral compounds) have been recently discovered. See, for example: U.S. patent application Ser. No. 08/850,398, filed May 2, 1997, by Webber et al.; U.S. patent application Ser. No. 08/991,282, filed Dec. 16, 1997, by Dragovich et al.; and U.S. patent application Ser. No. 08/991,739, filed Dec. 16, 1997, by Webber et al. These U.S. patent applications, the disclosures of which are incorporated herein by reference, describe certain antipicornaviral compounds and methods for their synthesis.

More recently, an especially potent group of antipicornaviral agents have been discovered as set forth in U.S. patent application Ser. No. 60/098,354, (the '354 application) filed Aug. 28, 1998, by Dragovich et al., which is herein incorporated by reference. This application discloses, inter alias, a group of antipicornaviral agents of general formula I. A particularly promising compound, AG7088, falling within the scope of this group, exhibits excellent antiviral properties against a plethora of Rhinoviral serotypes and is currently in human clinical trials. The '354 application also discloses methods and intermediates useful for synthesizing these compounds. For example, General Method V therein discloses a general method for synthesizing the compounds of formula I involving subjecting a carboxylic acid of general formula BB to an amide-forming reaction with an amine of general formula P to provide a final product CC, as shown below.

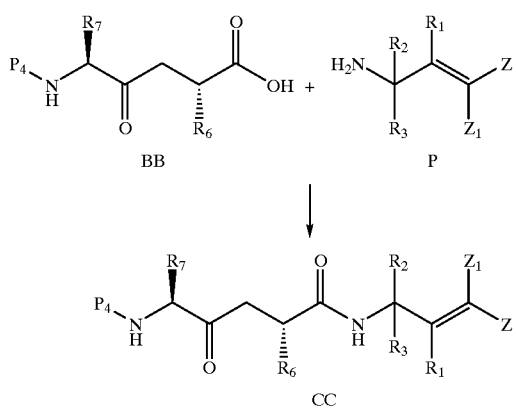

The '354 application further discloses methods for synthesizing the intermediates of general formulae BB and P, and teaches methods for carrying out the amide-forming reaction referred to above. Thus, the '354 application teaches suitable methods for synthesizing the compounds of general formula I from a carboxylic acid BB (within the scope of the compounds of general formula II referred to below) and the compounds of general formula P (the same as the compounds of general formula III referred to below.) Similarly, two recent publications by Dragovich et al. disclose antipicornavirus agents and suitable synthetic methods for their synthesis. See Structure-Based Design, Synthesis, and Biological Evaluation of Irreversable Human Rhinovirus 3C Proteases Inhibitors. 3. StructureActivity Studies of Ketomethylene-Containing Peptidonimietics, Dragovich et al., Journal of Medicinal Chemistry, ASAP, 1999; and Structure-Based Design, Synthesis, and Biological Evaluation of Irreversable Human Rhinovirus 3C Proteases Inhibitors. 4. Incorporation of P$_1$ Lactam Moieties as L-Glutamine Replacements, Dragovich et al., Journal of Medicinal Chemistry, ASAP, 1999. These aforementioned articles are herein incorporated by reference in their entirety.

However, there is still a desire to discover improved, more efficient, processes and novel intermediates for use in the syntheses of the compounds of the group of antipicornaviral agents. In particular, there is a need for improved methods for synthesizing the compounds of general formulae II and III.

SUMMARY OF THE INVENTION

The present invention relates to the discovery of a cost effective and efficient process for the preparation of the antipicornaviral agents of formula I, such as compound AG7088, as well as intermediates which are useful in that synthesis.

The antipicornaviral agents of formula I comprise:

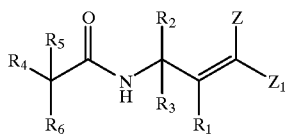

wherein $R_1$ is H, F, an alkyl group, OH, SH, or an O-alkyl group;

$R_2$ and $R_3$ are each independently H;

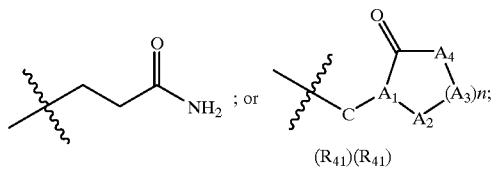

where n is an integer from 0 to 5, $A_1$ is CH or N, $A_2$ and each $A_3$ are independently selected from $C(R_{41})(R_{41})$, $N(R_{41})$, S, S(O), $S(O)_2$, and O and $A_4$ is NH or $NR_{41}$, where each $R_{41}$ is independently H or lower alkyl, provided that no more than two heteroatoms occur consecutively in the above-depicted ring formed by $A_1$, $A_2$, $(A_3)_n$, $A_4$ and C=O, and at least one of $R_2$ and $R_3$ is

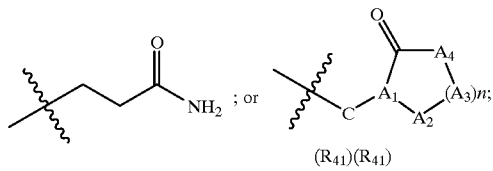

$R_4$ is

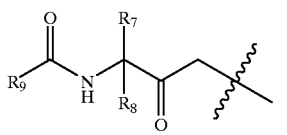

$R_5$ and $R_6$ are each independently H, F, an alkyl group, a cycloalkyl group, a heterocycloalkyl group, an aryl group, or a heteroaryl group;

$R_7$ and $R_8$ are each independently H, an alkyl group, a cycloalkyl group, a heterocycloalkyl group, an aryl group, a heteroaryl group, $-OR_{17}$, $-SR_{17}$, $-NR_{17}R_{18}$, $-NR_{19}NR_{17}R_{18}$, or $-NR_{17}OR_{18}$, where $R_{17}$, $R_{18}$, and $R_{19}$ are each independently H, an alkyl group, a cycloalkyl group, a heterocycloalkyl group, an aryl group, a heteroaryl group, or an acyl group, provided that at least one of $R_7$ and $R_8$ is an alkyl group, an aryl group, a heteroaryl group, $-OR_{17}$, $-SR_{17}$, $-NR_{17}R_{18}$, $-NR_{19}NR_{17}R_{18}$, or $-NR_{17}OR_{18}$; $R_9$ is a five-membered heterocycle having from one to three heteroatoms selected from O, N, and S; and Z and $Z_1$ are each independently H, F, an alkyl group, a cycloalkyl group, a heterocycloalkyl group, an aryl group, a heteroaryl group, $-C(O)R_{21}$, $-CO_2R_{21}$, CN, $-C(O)NR_{21}R_{22}$, $-C(O)NR_{21}OR_{22}$, $-C(S)R_{21}$, $-C(S)NR_{21}R_{22}$, $-NO_2$, $-SOR_{21}$, $-SO_2R_{21}$, $-SO_2NR_{21}R_{22}$, $-SO(NR_{21})(OR_{22})$, $-SONR_{21}$, $-SO_3R_{21}$, $-PO(OR_{21})_2$ $-PO(R_{21})(R_{22})$, $-PO(NR_{21}R_{22})(OR_{23})$, $-PO(NR_{21}R_{22})(NR_{23}R_{24})$, $-C(O)NR_{21}NR_{22}R_{23}$, or $-C(S)NR_{21}NR_{22}R_{23}$, where $R_{21}$, $R_{22}$, $R_{23}$, and $R_{24}$ are each independently H, an alkyl group, a cycloalkyl group, a heterocycloalkyl group, an aryl group, a heteroaryl group, an acyl group, or a thioacyl group, or where any two of $R_{21}$, $R_{22}$, $R_{23}$, and $R_{24}$, together with the atom(s) to which they are bonded, form a heterocycloalkyl group, provided that Z and $Z_1$ are not both H;

or $Z_1$ and $R_1$, together with the atoms to which they are bonded, form a cycloalkyl or heterocycloalkyl group, where $Z_1$ and $R_1$ are as defined above except for moieties that cannot form the cycloalkyl or heterocycloalkyl group;

or Z and $Z_1$, together with the atoms to which they are bonded, form a cycloalkyl or heterocycloalkyl group, where Z and $Z_1$ are as defined above except for moieties that cannot form the cycloalkyl or heterocycloalkyl group.

As discussed below, these antipicornaviral agents of formula I may be synthesized by subjecting a compound of general formula II together with a compound of general formula III to a suitable amide-forming reaction. The process of the present invention, not only reduces the number of steps required to synthesize the compounds of formula III, but more importantly, it also employs less expensive starting materials and reagents.

These objects, advantages and features of the present invention will be more fully understood and appreciated by reference to the written specification.

DETAILED DESCRIPTION OF A PREFERRED EMBODIMENT OF THE INVENTION

As used in the present application, the following definitions apply:

In accordance with a convention used in the art,

is used in structural formulas herein to depict the bond that is the point of attachment of the moiety or substituent to the core or backbone structure.

Where chiral carbons are included in chemical structures, unless a particular orientation is depicted, both sterioisomeric forms are intended to be encompassed.

An "alkyl group" is intended to mean a straight or branched chain monovalent radical of saturated and/or unsaturated carbon atoms and hydrogen atoms, such as methyl (Me), ethyl (Et), propyl, isopropyl, butyl (Bu), isobutyl, t-butyl (t-Bu), ethenyl, pentenyl, butenyl, propenyl, ethynyl, butynyl, propynyl, pentynyl, hexynyl, and the like, which may be unsubstituted (i.e., containing only carbon and hydrogen) or substituted by one or more suitable substituents as defined below (e.g., one or more halogens, such as F, Cl, Br, or I, with F and Cl being prefered). A "lower alkyl group" is intended to mean an alkyl group having from 1 to 4 carbon atoms in its chain.

A "cycloalkyl group" is intended to mean a non-aromatic monovalent monocyclic, bicyclic, or tricyclic radical containing 3, 4, 5, 6, 7, 8, 9, 10, 11, 12, 13, or 14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more substituents. Illustrative examples of cycloalkyl groups include the following moieties:

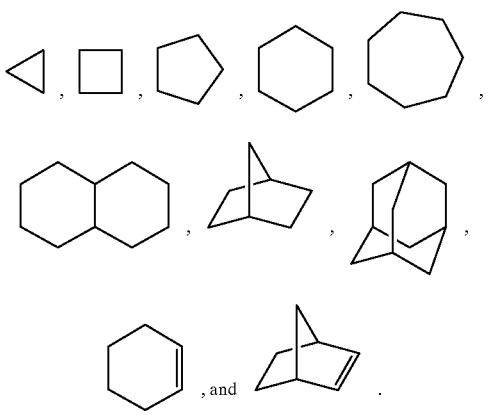

A "heterocycloalky group" is intended to mean a non-aromatic monovalent monocyclic, bicyclic, or tricyclic radical, which is saturated or unsaturated, containing 3, 4, 5, 6, 7, 8, 9, 10, 11, 12, 13, 14, 15, 16, 17, or 18 ring atoms, which includes 1, 2, 3, 4, or 5 heteroatoms selected nitrogen, oxygen, and sulfur, where the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include the following moieties:

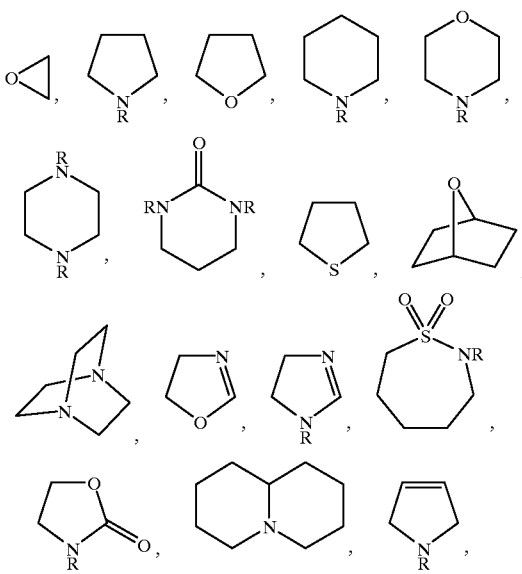

-continued

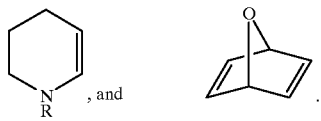

An "aryl group" is intended to mean an aromatic monovalent monocyclic, bicyclic, or tricyclic radical containing 6, 10, 14 or 18 carbon ring atoms, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Illustrative examples of aryl groups include the following moieties:

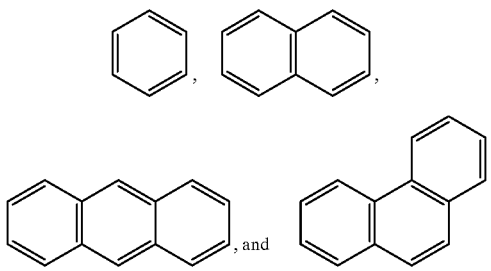

A "heteroaryl group" is intended to mean an aromatic monovalent monocyclic, bicyclic, or tricyclic radical containing 4, 5, 6, 7, 8, 9, 10, 11, 12, 13, 14, 15, 16, 17, or 18 ring atoms, including 1, 2, 3, 4, or 5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include the following moieties:

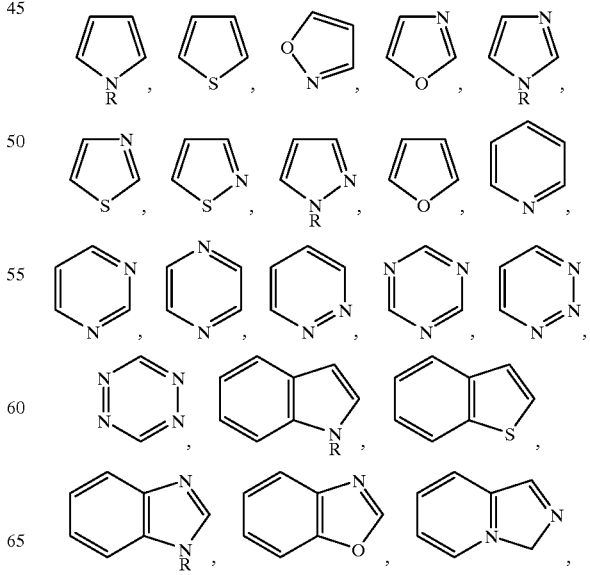

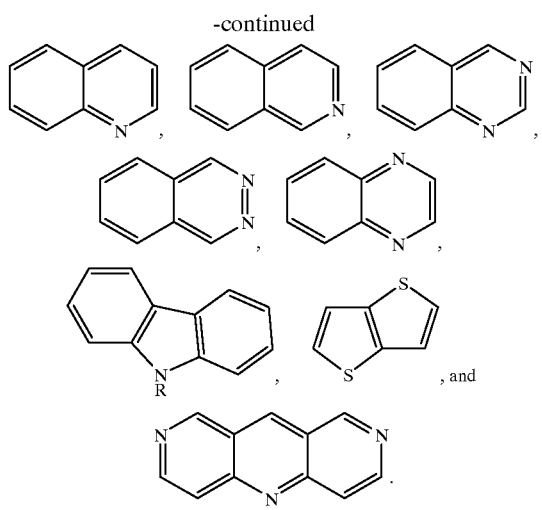

A "heterocycle" is intended to mean a heteroaryl or heterocycloalkyl group (each of which, as defined above, are optionally substituted).

An "acyl group" is intended to mean a —C(O)—R radical, where R is a substituent as defined below.

A "thioacyl group" is intended to mean a —C(S)—R radical, where R is a substituent as defined below.

A "sulfonyl group" is intended to mean a —SO$_2$R radical, where R is a substituent as defined below.

A "hydroxy group" is intended to mean the radical —OH.

An "amino group" is intended to mean the radical —NH$_2$.

An "alkylamino group" is intended to mean the radical —NHR$_a$, where R$_a$ is an alkyl group.

A "dialkylamino group" is intended to mean the radical —NR$_a$R$_b$, where R$_a$ and R$_b$ are each independently an alkyl group.

An "alkoxy group" is intended to mean the radical —OR$_a$, where R$_a$ is an alkyl group. Exemplary alkoxy groups include methoxy, ethoxy, propoxy, and the like.

An "alkoxycarbonyl group" is intended to mean the radical —C(O)OR$_a$, where R$_a$ is an alkyl group.

An "alkylsulfonyl group" is intended to mean the radical —SO$_2$R$_a$, where R$_a$ is an alkyl group.

An "alkylaminocarbonyl group" is intended to mean the radical —C(O)NHR$_a$, where R$_a$ is an alkyl group.

A "dialkylaminocarbonyl group" is intended to mean the radical —C(O)NR$_a$R$_b$, where R$_a$ and R$_b$ are each independently an alkyl group.

A "mercapto group" is intended to mean the radical —SH.

An "alkylthio group" is intended to mean the radical —SR$_a$, where R$_a$ is an alkyl group.

A "carboxy group" is intended to mean the radical —C(O)OH.

A "carbamoyl group" is intended to mean the radical —C(O)NH$_2$.

An "aryloxy group" is intended to mean the radical —OR$_c$, where R$_c$ is an aryl group.

A "heteroaryloxy group" is intended to mean the radical —OR$_d$, where R$_d$ is a heteroaryl group.

An "arylthio group" is intended to mean the radical —SR$_c$, where R$_c$ is an aryl group.

A "heteroarylthio group" is intended to mean the radical —SR$_d$, where R$_d$ is a heteroaryl group.

A "leaving group" (Lv) is intended to mean any suitable group that will be displaced by a substitution reaction. One of ordinary skill in the art will know that any conjugate base of a strong acid can act as a leaving group. Illustrative examples of suitable leaving groups include, but are not limited to, —F, —Cl, —Br, alkyl chlorides, alkyl bromides, alkyl iodides, alkyl sulfonates, alkyl benzenesulfonates, alkyl p-toluenesulfonates, alkyl methanesulfonates, triflate, and any groups having a bisulfate, methyl sulfate, or sulfonate ion.

Typical protecting groups, reagents and solvents such as, but not limited to, those listed below in table 1 have the following abbreviations as used herein and in the claims. One skilled in the art would understand that the compounds listed within each group may be used interchangeably; for instance, a compound listed under "reagents and solvents" may be used as a protecting group, and so on. Further, one skilled in the art would know other possible protecting groups, reagents and solvents; these are intended to be within the scope of this invention.

TABLE 1

| Protecting Groups | |
|---|---|
| Ada | Adamantane acetyl |
| Alloc | Allyloxycarbonyl |
| Allyl | Allyl ester |
| Boc | tert-butyloxycarbonyl |
| Bzl | Benzyl |
| Cbz | Benzyloxycarbonyl |
| Fmoc | Fluorenylmethyloxycarbonyl |
| OBzl | Benzyl ester |
| OEt | Ethyl ester |
| OMe | Methyl ester |
| Tos (Tosyl) | p-Toluenesulfonyl |
| Trt | Triphenylmethyl |

| Reagents and Solvents | |
|---|---|
| ACN | Acetonitrile |
| AcOH | Acetic acid |
| Ac.sub.2 O | Acetic acid anhydride |
| AdacOH | Adamantane acetic acid |
| AIBN | 2,2-azobisisobutyronitrile |
| Alloc-Cl | Allyloxycarbonyl chloride |
| BHT | 2,6-di-tert-butyl-4-methylphenol |
| Boc.sub.2 O | Di-tert butyl dicarbonate |
| CDI | 1,1'-carbonyldiimidazole |
| DIEA | Diisopropylethylamine |
| DIPEA | N,N-diisopropylethylamine |
| DMA | Dimethylacetamide |
| DMF | N,N-dimethylformamide |
| DMSO | Dimethyl sulfoxide |
| EDTA | ethylenediaminetetraacetic acid |
| Et.sub.3 N | Triethylamine |
| EtOAc | Ethyl acetate |
| FDH | formate dehydrogenase |
| FmocOSu | 9-fluorenylmethyloxy carbonyl N-hydroxysuccinimide ester |
| HATU | N-[(dimethylamino)-1H-1,2,3-triazol[4,5-b]pyridiylmethylene]-N-methylmethanaminium hexafluorophosphate N-oxide |
| HOBT | 1-Hydroxybenzotriazole |
| HF | Hydrofluoric acid |
| LDH | lactate dehydrogenase |
| LiHMDS | Lithium bistrimethylsilylamide |
| MeOH | Methanol |
| Mes (Mesyl) | Methanesulfonyl |
| MTBE | t-butyl methyl ether |
| NAD | Nicotinamide adenine dinucleotide |
| NADH | Hydrogen-peroxide oxidoreductase |
| NaHMDS | Sodium bistrimethylsilylamide |
| NMP | 1-methyl-2-pyrrolidinone |
| nin. | Ninhydrin |
| i-PrOH | Iso-propanol |
| Pip | Piperidine |
| PPL | Lipase |
| pTSA | p-toluensulfonic acid monohydrate |
| Pyr | Pyridine |
| TEA | Triethylamine |
| TET | triethylenetetraamine |

TABLE 1-continued

| | |
|---|---|
| TFA | Trifluoroacetic acid |
| THF | Tetrahydrofuran |
| Triflate (Tf) | Trifluoromethanesulfonyl |

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxyl groups, alkyl groups, oxo groups, cycloalkyl groups, heterocycloalkyl groups, aryl groups, heteroaryl groups, acyl groups, sulfonyl groups, mercapto groups, alkylthio groups, alkoxy groups, carboxy groups, amino groups, alkylamino groups, dialkylamino groups, carbamoyl groups, arylthio groups, heteroarylthio groups, and the like.

The term "substituent" or "suitable substituent" is intended to mean any suitable substituent that may be recognized or selected, such as through routine testing, by those skilled in the art. Illustrative examples of suitable substituents include hydroxy groups, halogens, oxo groups, alkyl groups, acyl groups, sulfonyl groups, mercapto groups, alkylthio groups, alkyloxy groups, cycloalkyl groups, heterocycloalkyl groups, aryl groups, heteroaryl groups, carboxy groups, amino groups, alkylamino groups, dialkylamino groups, carbamoyl groups, aryloxy groups, heteroaryloxy groups, arylthio groups, heteroarylthio groups, and the like.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

A "prodrug" is intended to mean a compound that is converted under physiological conditions or by solvolysis or metabolically to a specified compound that is pharmaceutically active.

A "pharmaceutically active metabolite" is intended to mean a pharmacologically active product produced through metabolism in the body of a specified compound.

A "solvate" is intended to mean a pharmaceutically acceptable solvate form of a specified compound that retains the biological effectiveness of such compound. Examples of solvates include compounds of the invention in combination with water, isopropanol, ethanol, methanol, DMSO, ethyl acetate, acetic acid, or ethanolamine.

A "pharmaceutically acceptable salt" is intended to mean a salt that retains the biological effectiveness of the free acids and bases of the specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophaosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phylacetates, phenylpropionates, phylbutyrates, citrates, lactates, γ-hydroxybutyrates, glycollates, tartrates, methanesulfonates, propanesulfonates, naphthalene-1-sulfonates, naphthalene-2-sulfonates, and mandelates.

The present invention further provides synthetic methods that are comprised of one of the synthetic steps set forth in the present disclosure. A synthetic method is comprised of a synthetic step when the synthetic step is at least part of the final synthetic method. In such a fashion, the synthetic method can be only the synthetic step or have additional synthetic steps that may be associated with it. Such a synthetic method can have a few additional synthetic steps or can have numerous additional synthetic steps.

If the antipicornaviral agent of formula I formed from the process of the present invention is a base, a desired salt may be prepared by any suitable method known to the art, including treatment of the free base with an inorganic acid, such as hydrochloric acid; hydrobromic acid; sulfuric acid; nitric acid; phosphoric acid; and the like, or with an organic acid, such as acetic acid; maleic acid; succinic acid; mandelic acid; fumaric acid; malonic acid; pyruvic acid; oxalic acid; glycolic acid; salicylic acid; pyranosidyl acid, such as glucuronic acid or galacturonic acid; alpha-hydroxy acid, such as citric acid or tartaric acid; amino acid, such as aspartic acid or glutamic acid; aromatic acid, such as benzoic acid or cinnamic acid; sulfonic acid, such as p-toluenesulfonic acid or ethanesulfonic acid; or the like.

If the antipicornaviral agent of formula I formed from the process of the present invention is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

In the case of compounds, salts, or solvates that are solids, it is understood by those skilled in the art that the compounds of formula I and the intermediates used in the process of the present invention, salts, and solvates thereof, may exist in different crystal forms, all of which are intended to be within the scope of the present invention and specified formulas.

The antipicornaviral agents of formula I, and the intermediates used in the process of the present invention, may exist as single stereoisomers, racemates, and/or mixtures of enantiometers and/or diastereomers. All such single stereoisomers, racemates, and mixtures thereof are intended to be within the broad scope of the present invention. Preferably, however, the intermediate compounds used in the process of the present invention are used in optically pure form.

As generally understood by those skilled in the art, an optically pure compound is one that is enantiomerically pure. As used herein, the term "optically pure" is intended to mean a compound comprising at least a sufficient amount of a single enantiomer to yield a compound having the desired pharmacological activity. Preferably, "optically pure" is intended to mean a compound that comprises at least 90% of a single isomer (80% enantiomeric excess (hereinafter "e.e.")), more preferably at least 95% (90% e.e.), even more preferably at least 97.5% (95% e.e.), and most preferably at least 99% (98% e.e.) Preferably, the antipicornaviral agents of formula I formed from the process of the present invention are optically pure.

The present invention relates to a process of preparing antipicornaviral agents of formula I:

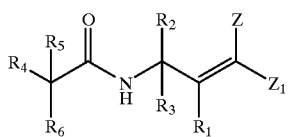

(I)

wherein $R_1$ is H, F, an alkyl group, OH, SH, or an O-alkyl group;
$R_2$ and $R_3$ are each independently H;

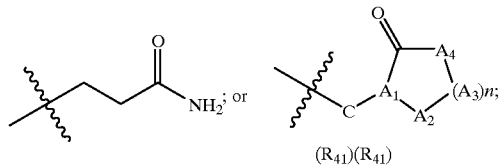

where n is an integer from 0 to 5, $A_1$ is CH or N, $A_2$ and each $A_3$ are independently selected from $C(R_{41})(R_{41})$, $N(R_{41})$, S, S(O), S(O)$_2$, and O, and $A_4$ is NH or $NR_{41}$, where each $R_{41}$ is independently H or lower alkyl, provided that no more than two heteroatoms occur consecutively in the above-depicted ring formed by $A_1$, $A_2$, $(A_3)_n$, $A_4$ and C=O, and at least one of $R_2$ and $R_3$ is

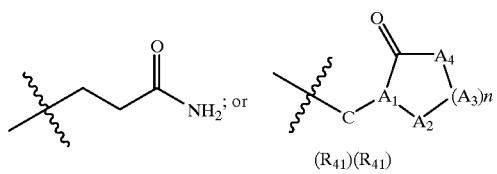

$R_4$ is

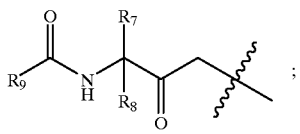

$R_5$ and $R_6$ are each independently H, F, an alkyl group, a cycloalkyl group, a heterocycloalkyl group, an aryl group, or a heteroaryl group;

$R_7$ and $R_8$ are each independently H, an alkyl group, a cycloalkyl group, a heterocycloalkyl group, an aryl group, a heteroaryl group, $-OR_{17}$, $-SR_{17}$, $-NR_{17}R_{18}$, $-NR_{19}NR_{17}R_{18}$, or $-NR_{17}OR_{18}$, where $R_{17}$, $R_{18}$, and $Rl_{19}$ are each independently H, an alkyl group, a cycloalkyl group, a heterocycloalkyl group, an aryl group, a heteroaryl group, or an acyl group, provided that at least one of $R_7$ and $R_8$ is an alkyl group, an aryl group, a heteroaryl group, $-OR_{17}$, $-SR_{17}$, $-NR_{17}R_{18}$—$NR_{19}NR_{17}R_{18}$, or $-NR_{17}OR_{18}$; $R_9$ is a five-membered heterocycle having from one to three heteroatoms selected from O, N, and S; and Z and $Z_1$ are each independently H, F, an alkyl group, a cycloalkyl group, a heterocycloalkyl group, an aryl group, a heteroaryl group, $-C(O)R_{21}$, $-CO_2R_{21}$, CN, $-C(O)NR_{21}R_{22}$, $-C(O)NR_{21}OR_{22}$, $-C(S)R_{21}$, $-C(S)NR_{21}R_{22}$, $-NO_2$, $-SOR_{21}$, $-SO_2R_{21}$, $-SO_2NR_{21}R_{22}$, $-SO(NR_{21})(OR_{22})$, $-SONR_{21}$, $-SO_3,R_{21}$, $-PO(OR_{21})_2$, $-PO(R_{21})(R_{22})$, $-PO(NR_{21}R_{22})(OR_{23})$, $-PO(NR21R_{22})(NR_{23}R_{24})$, $-C(O)NR_{21}NR_{22}R_{23}$, or $-C(S)NR_{21}NR_{22}R_{23}$, where $R_{21}$, $R_{22}$, $R_{23}$, and $R_{24}$ are each independently H, an alkyl group, a cycloalkyl group, a heterocycloalkyl group, an aryl group, a heteroaryl group, an acyl group, or a thioacyl group, or where any of two of $R_{21}$, $R_{22}$, $R_{23}$, and $R_{24}$, together with the atom(s) to which they are bonded, form a heterocycloalkyl group, provided that Z and $Z_1$ are not both H;

or $Z_1$ and $R_1$, together with the atoms to which they are bonded, form a cycloalkyl or heterocycloalkyl group, where $Z_1$ and $R_1$ are as defined above except for moieties that cannot form the cycloalkyl or heterocycloalkyl group;

or Z and $Z_1$, together with the atoms to which they are bonded, form a cycloalkyl or heterocycloalkyl group, where Z and $Z_1$ are as defined above except for moieties that cannot form the cycloalkyl or heterocycloalkyl group.

The present invention discloses that a compound of formula I may be prepared by subjecting a compound of formula II and a compound of formula III to a amide-forming reaction:

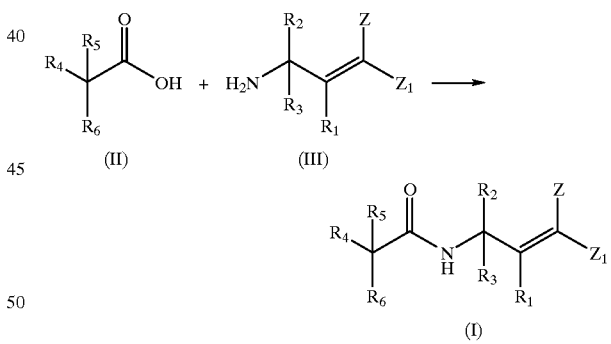

The amide-forming reaction may be achieved by any suitable method, reagents and reaction conditions. Preferably, any one of the methods disclosed in the '354 application is utilized. For example, a compound of formula II may be reacted with a compound of formula III in the presence of HATU, DIPEA, $CH_3CN$ and $H_2O$ to yield desired compound of formula I. Any suitable purification method may be used to further purify the compound of formula I.

More preferably, the compound of formula I is prepared by an amide-forming reaction comprising the steps of:

(a) reacting the compound of formula II with a compound of formula IIIA in the presence of N-methylmorpholine to form a reaction mixture; and

(IIIA)

(b) adding a compound of formula Lv-X to the reaction mixture to form a compound of formula I, wherein X is any suitable halide.

Preferably, the method for preparing the compound of formula I utilizing the more preferable amide-forming reaction utilizes some or all of the reagents and reaction conditions disclosed below. Thus, preferably, the compound of formula II and the compound of formula IIIA in DMF are combined in any suitable container. The suitable container is preferably a single neck flask which is then covered with any suitable septum and covered with a temperature probe. Nitrogen gas is used to purge out the suitable container before N-methylmorpholine is added to the reaction mixture. More preferably, the N-methylmorpholine is added via a syringe in one single portion and the reaction mixture cooled to about between −5° C. and 5° C. More preferably, the reaction mixture is cooled to about 0° C. A solution of the compound of formula Lv-X is then added to the reaction mixture. More preferably, the solution of the compound of formula Lv-X is a solution of the compound of formula Lv-X in DMF. Even more preferably, the compound of formula Lv-X is CDMT. The solution of the compound of formula Lv-X is added to the reaction mixture by any suitable method so as to maintain the reaction mixture at a constant temperature. For example, the solution of the compound of formula Lv-X may be added to the reaction mixture dropwise utilizing a syringe. Upon completion of the addition of the solution of the compound of formula Lv-X, the reaction mixture is allowed to warm to about room temperature. The progress of the reaction may be followed by monitoring the disappearance of the compound of formula II by thin layer chromatography (hereinafter "TLC"). When the reaction is at least substantially complete, the compound of formula I may be precipitated out of solution to form a slurry by slowly adding water to the reaction mixture. The compound of formula I may then be removed from the slurry by any suitable means known to one of ordinary skill in the art. For example, the compound of formula I may be removed from the slurry by filtration. Any suitable purification method known to one of ordinary skill in the art may be used to purify the compound of formula I. More preferably, the compound of formula I is purified by recrystalization.

The present invention also discloses two alternate processes for the synthesis of the compound of formula III and acid addition salts thereof. Of these two routes, the second process is currently preferred because it offers greater cost-effectiveness at a commercial scale.

The first of these two processes is for the preparation of a compound of formula IV and its acid addition salts from a compound of formula V.

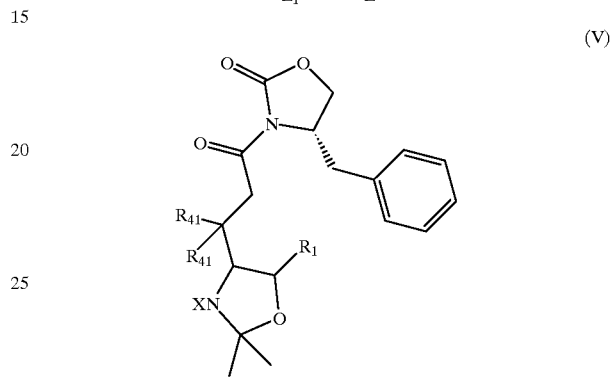

One of ordinary skill will recognize that the compounds of formula IV are a subgenus to those of formula III.

The compound of formula V may be prepared from commercially available N-Boc L glutanic acid γ-benzyl ester. Any suitable method may be used to prepare the compound of formula V. Preferably, the method disclosed in U.S. patent application Ser. No. 08/991,739 is used. U.S. patent application Ser. No. 08/991,739 is herein incorporated by reference in its entirety.

The process of the present invention comprises the steps of:

(a) cyanomethylation of the compound of formula V using bis(trimethysily)amide and bromoacetonitrile to yield a compound of formula VI;

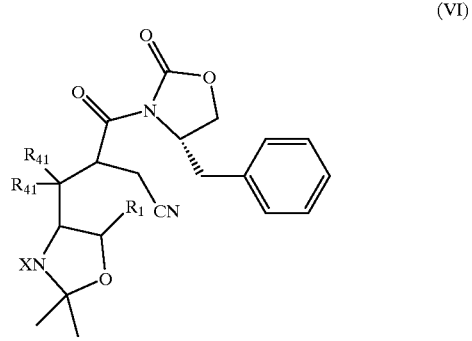

(b) the reduction, cyclization, and deprotection of the compound of formula VI in that respective order to yield a compound of formula VII; and

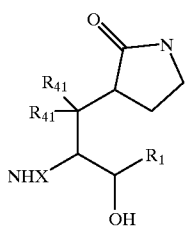

(VII)

(c) the oxidation and olefination of the compound of formula VII by reacting the compound with a $SO_3$-pyridine complex to yield a reaction mixture and reacting the reaction mixture with a phosphorane of formula VIII.

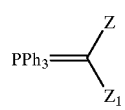

(VIII)

According to the present invention, and as disclosed above, the preparation of the compound of formula V from N-Boc glutanic acid γ-benzyl ester may be carried out by any suitable method known in the art.

Further, the cyanomethylation of the compound of formula V may be carried out using any suitable method, reagents and reaction conditions. Preferably, the method disclosed below and the use of all or some of the reagents and reaction conditions are used. Thus, it is preferable, that the compound of formula V be added dropwise to a stirring solution of NaHMDS in THF at −70° C. in a nitrogen atmosphere over a period of at least about 5 hours before being mixed with bromoacetonitrile.

This cyanomethylation of the compound of formula V using bis(trimethylsilyl)amide and bromoacetonitrile affords the compound of formula VI along with its epimer in a 5:1 ratio. However, the compound may be purified by any suitable method. Preferably, the compound of formula VI is purified by filtration and chromatography, followed by titration. Under these preferred conditions, a 60% overall yield of the compound of formula VI is attainable having >99% diastereomeric purity.

The three step reduction, cyclization, and deprotection reaction of step (b) to convert the compound of formula VI to the compound of formula VII may be carried out using any suitable reagents and reaction conditions. Preferably, the method disclosed below, using all or some of the reagents and reaction conditions are used. Therefore, preferably, the compound of formula VI is reduced by adding a solution of cobalt (II) chloride hexahydrate to a solution of the compound of formula VI in tetrahydrofuran in methanol. The resulting solution is cooled to about 0° C. before sodium borohydride is added in portions over a period of at least about 7 hours. Then, p-toluensulfonic acid monohydrate is added to the solution of crude material in methanol and allowed to react for at least about 18 hours at an ambient temperature. After removal of the solvent, the residue is dissolved in ethyl acetate and washed. Any suitable washing agent may be used. More preferably, the washing agent is saturated sodium bicarbonate. The crude product is then charged with a solution of methanol in water. More preferably, a 2.5% methanol solution is used. The crude product may be removed from solution by any suitable method. For example, the crude product may be removed by filtration and the filtrate concentrated on a rotary evaporator. The product is then dissolved in ethyl acetate, dried, filtered and concentrated to the crude compound of formula VII. More preferably, the product is dried over $MgSO_4$. The crude compound of formula VII may be further purified by any suitable purification process. More preferably, the crude compound of formula VII is purified through a titration process using 1:1 ethyl acetate and hexanes.

An overall yield of at least about 95% pure compound of formula VII is attainable if the preferred three step reduction, cyclization, and deprotection reaction disclosed above is used.

Any suitable method, reagents and reaction conditions may be used in the subsequent oxidation and olefination employing a $SO_3$-pyridine complex and the phosphorane of formula VIII to yield the compound of formula IV. Preferably, the method disclosed below and all or some of the reagents and reaction conditions are used. Accordingly, preferably, triethylamine is added to a solution of the compound of formula VIII and methylsulfoxide. The resulting solution is cooled to about 5° C., followed by the addition of a sulfur trioxide-pyridine complex. The reaction is stirred at about 5° C. for at least about 15 minutes. After removing the source used to cool the solution to about 5° C., the reaction is stirred for at least about an additional 1 hour. (Carboethoxymethylenetriphenyl)-phosphorane is then added and the reaction mixture stirred at ambient temperature for at least about 3 hours. Then, the reaction is quenched and extracted with ethyl acetate. More preferably, the reaction is quenched by the addition of saturated brine. The combined organic phases are then washed, dried, filtered and concentrated to afford crude compound of formula IV. More preferably, the combined organic phases are washed with saturated brine and dried over $MgSO_4$.

The compound of formula IV may be purified by any suitable method. Preferably, chromatography purification and titration techniques are used. If the preferable purification technique is used, yields ranging from 55% to 60% are attainable.

The second process for preparing the compound of formula IV, and its acid addition salts, disclosed by the present invention comprises the steps of:

(a) the dianionic alkylation of a compound of formula IX using bromoacetonitrile to yield a compound of formula X;

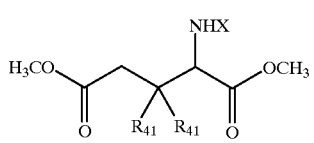

(IX)

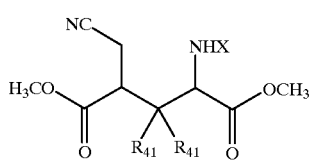

(X)

(b) hydrogenation of the compound of formula X to yield an amine of formula XI;

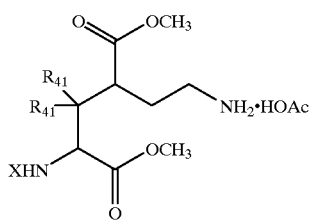

(XI)

(c) reacting the amine of formula XI with ET$_3$N to yield a lactam ester of formula XII;

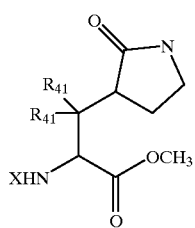

(XII)

(d) the reduction of the lactam ester of formula XII through a suitable reduction procedure to yield a compound of formula XIII;

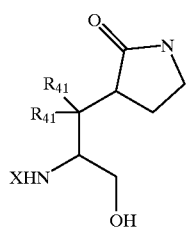

(XIII)

(e) the oxidation and olefination of the compound of formula XIII to yield a compound of formula XIV by reacting it with a compound of formula XV; and

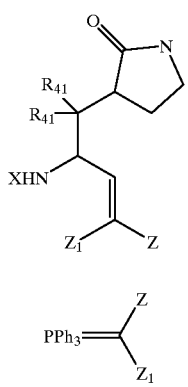

(XIV)

(XV)

(f) converting the compound of formula XIV to the compound of formula IV.

Further, one of ordinary skill in the art will realize that the above disclosed method may be used to prepare the compound of formula XIV. Specifically, steps (a)–(e) disclose a process for preparing the compound of formula XIV.

The compound of formula IX may be prepared by any suitable method known in the art. For example, N-Boc L-(+)-glutamic acid dimethyl ester may be prepared from commercially available L-glutamic acid dimethyl ester hydrochloride or commercially available L-glutamic acid 5-methyl ester according to literature procedures. See for example, Shimamoto et al, J. Org. Chem. 1991, 56, 4167 and Duralski et al, Tetrahedron Lett. 1998, 30, 3585. These references are herein incorporated by reference in their entirety.

Preferably, the dianionic alkylation reaction is performed using the method and all or some of the reagents and reaction conditions disclosed below. Therefore, preferably, the compound of formula IX is first dissolved in THF to form a solution which is added dropwise to a stirring solution of LiHMDS at −78° C. in an Argon atmosphere. The resulting mixture is then stirred at about −78° C. for 2 hours before freshly distilled bromoacetonitrile is added dropwise over a period of 1 hour. The reaction mixture is stirred at about −78° C. for additional 2 hours. The reaction is then quenched. More preferably, the reaction is quenched by adding 0.5 M HCl and H$_2$O. The resulting aqueous layer is separated and is extracted further with methyl tert-butyl ether. The combined organic extract is washed, dried and filtered. More preferably, the organic extract is washed with saturated NaHCO$_3$ and brine and dried over MgSO$_4$. The solvent is evaporated under reduced pressure.

The compound of formula IX may be hydrogenated to the amine of formula XI by any suitable method known in the art. Preferably, the hydrogenation is performed in the presence of 5% Pd/C. More preferably, the hydrogenation reaction is performed in accordance with the method, using some or all of the reagents and reaction conditions disclosed below. According to this preferred hydrogenation method, the compound of formula IX is dissolved in HOAc and shaken with 5% Pd on C under H$_2$ gas, at 50 psi pressure, for 3 days. The mixture is then filtered over celite. The filtrate may then be evaporated under reduced pressure and the residue repeatedly evaporated from methyl tert-butyl ether.

The reaction of the amine of formula XI with Et$_3$N may be achieved using any suitable conditions. Preferably, the method and all or some of the reagents and reaction conditions disclosed below are used. Accordingly, preferably, the amine of formula XI is dissolved in 1:1 MeOH/THF, before Et$_3$N is added to the solution. The resulting mixture is stirred at about 45° C. for about 10 hours or until the starting material has disappeared. The presence of the starting material may be monitored by $^1$H NMR. After stripping off the solvent, methyl tert-butyl ether is added. The precipitate is then filtered. 0.5 M HCl is added to the filtrate diluted with H$_2$O. After splitting the phases, the aqueous phase may be extracted with ethyl acetate. The combined organic phases are washed, dried, filtered and concentrated. More preferably, the combined organic phases are washed with brine and dried over MgSO$_4$. The phases may be concentrated on a rotovapor. Flash chromatography furnishes the lactam ester of formula XII.

Any suitable reduction method may be used to convert the lactam ester of formula XII to the compound of formula XIII. Preferably, LiBH$_4$ is used as the reducing agent. More preferably, the method, or any portion thereof, and any or all of the reagents and reaction conditions disclosed below are used. Thus, more preferably, LiBH$_4$ is added to a stirring solution of the lactam ester of formula XII in THF. The LiBH$_4$ is added in several portions at 0° C. in an Argon atmosphere. The reaction mixture is stirred at 0° C. for 10 minutes, before being allowed to warm to ambient temperature and stirred for an additional 2 hours. Then, the reaction is quenched. Even more preferably, the reaction is quenched by the dropwise addition of 0.5 M HCl while cooling using an ice bath. The solution is diluted with ethyl acetate and H$_2$O. After splitting the phases, the aqueous phase may be extracted with ethyl acetate. The combined organic phases are washed, dried, filtered and concentrated. Even more preferably, the combined organic phases are washed with brine and dried over MgSO$_4$. The phases may be concentrated on a rotovapor. Flash chromatography furnishes the compound of formula XII.

Any suitable oxidation and olefination method may be used to prepare the compound of formula XIV from the compound of formula XIII. Preferably, the method, or any part thereof, and all or some of the reagents and reaction conditions described below are used. Thus, in accordance with the present invention, benzoic acid, (carboethoxymethylenetriphenyl)phosphorane and DMSO are added to a solution of the compound of formula XIII in CH$_2$Cl$_2$. Dess-Martin periodinane is added to the solution in several portions, and the reaction mixture is then stirred for at least about 5 hours at ambient temperature until the compound of formula XIII substantially disappears. The presence of the compound of formula XIII may be monitored by $^1$H NMR. Saturated NaHCO$_3$ solution is added before the mixture is stirred for 30 minutes to yield a precipitate. The precipitate is filtered prior to the organic phase of the filtrate being separated, washed, and concentrated to yield the crude compound of formula XIV. More preferably, the filtrate is washed with brine and concentrated on a rotovapor. Any suitable method may be used to purify the crude compound of formula XIV. More preferably, the crude compound of formula XIV is purified by flash chromatography, then dissolved in ethyl acetate. Excess hexanes are then added gradually to the stirring solution to yield a precipitated. The precipitate is filtered and dried to afford the compound of formula XIV. More preferably, the precipitate is dried in a vacuum oven for at least about 12 hours.

The following examples are provided merely for illustrative purposes of the present invention and are not to be read as limiting the scope of protection of the present invention, as defined by the appended claims.

EXAMPLES

The following illustrates an example of the amide-forming reaction between two compounds falling within the scope of formulae II and III to prepare a compound falling within the scope of formula I. Specifically, this example, as depicted in Scheme 1 below, illustrates the reaction of 1 with 2 to prepare the protease inhibitor AG7088.

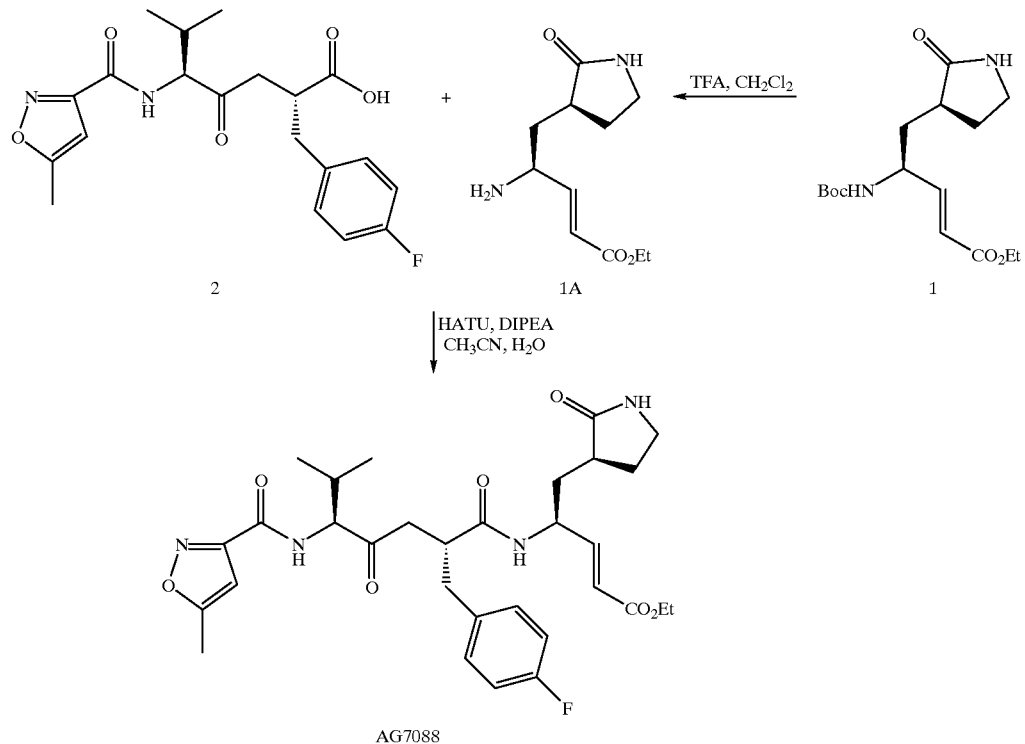

Scheme 1

The following examples disclose the preparation of compound 1 falling within the scope of formula IV. The first example, as depicted in Scheme 2 below, illustrates the use of the cyanomethylation route disclosed above. The second example, depicted in Scheme 3 below, illustrates the second more preferable cost effective route for preparing the same compound.

Scheme 2
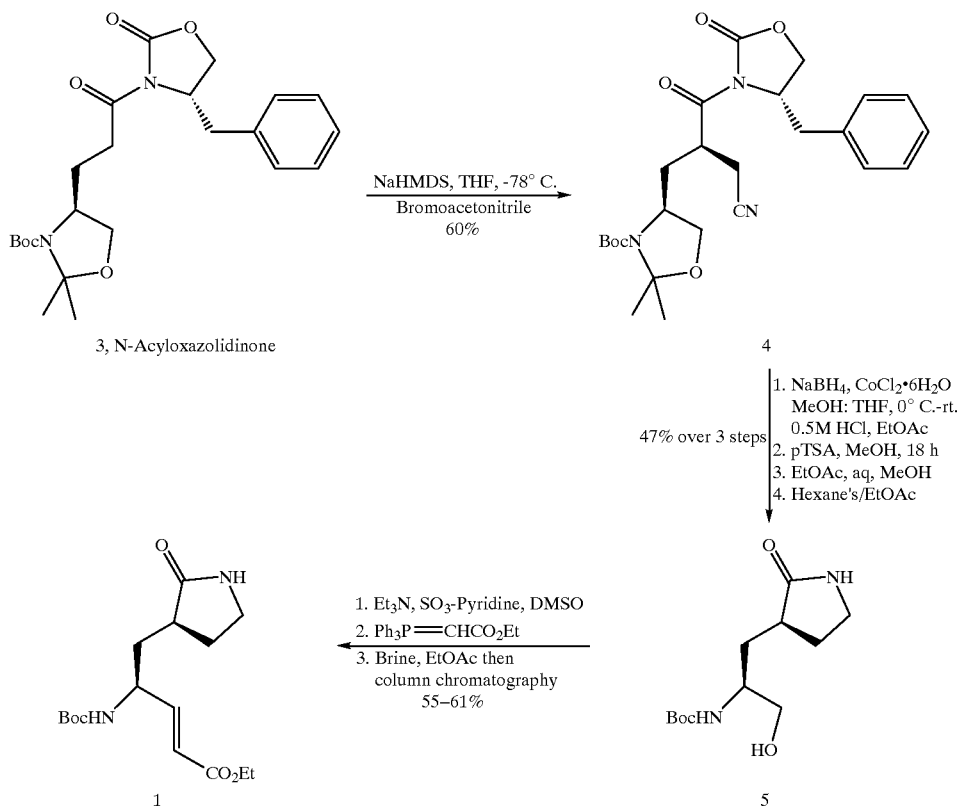
Scheme 3
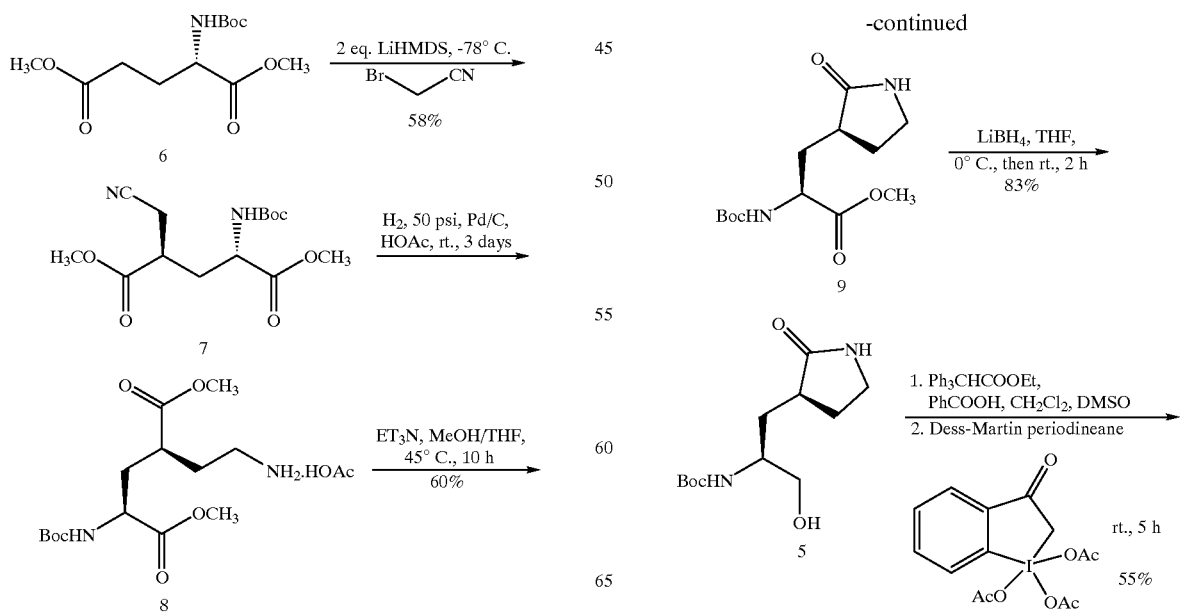

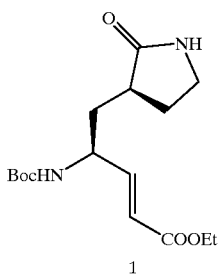

Preparation of 4 (Scheme 2)

A solution of 3 (1.0 k, 2.34 mol, 1.0 equiv.) in THF (8.0 L) was added dropwise to a stirring solution of NaHMDS in THF (1M in THF, 2.96 L, 1.28 equiv.) at −70° C. in a nitrogen atmosphere over a period of 5 hours. The resulting solution was stirred at −70° C. for 0.5 hours and freshly distilled bromoacetonitrile (320 mL, 2.0 equiv.) was then added dropwise over a period of 25 minutes. The reaction mixture was stirred at −70° C. for additional 1 hour until the disappearance of the starting material 3. The reaction was quenched by addition of saturated ammonium chloride solution (7.0 L), and extracted with methyl tert-butyl ether (24 L). The organic phase was washed with brine (3×6.0 L). The solvent was removed under reduce pressure to afford a dark brown oil (1.5 kg). This crude product was dissolved in methylene chloride (8.0 L) and passed over a bed of silical gel (600 g) and activated carbon (250 g). After rinsing the cake with methylene chloride (4.0 L), the filtrate was concentrated on a rotary evaporator to afford a light brown oil (1,28 Kg), which was then dissolved in ethyl acetate (2.5 L). To the resulting solution, excess hexanes (14.5 L) were added under vigorous stirring and a white solid precipitated out in 30 minutes. The slurry was cooled with an ice-water bath and stirred for 4.5 hours, followed by filtration to afford 4 as a light brown solid (662 g, 60%): $^1$H NMR (CDCl$_3$) δ1.46 (s, 3 H), 1.49 (s, 9 H), 1.59 (s, 3 H), 1.75–1.95 (m, 1 H), 2.15–2.31 (m, 1 H), 2.55–3.15 (m, 3 H), 3.36 (d,J=10.8 Hz, 1 H), 3.62–4.10 (m, 3 H), 4.13–4.32 (m, 3 H), 4.70 (m, 1 H), 7.15–7.42 (m, 5 H).

Preparation of 6 (Scheme 3)

Compound 6 was prepared from L-glutamic acid dimethyl ester hydrochloride (commercially available from Lancaster) or L-glutamic acid 5-methyl ester (commercially available from Aldrich) according to literature procedures.

Preparation of 7 (Scheme 3)

A solution of N-Boc L-(+)-glutamic acid dimethyl ester (6, 10 g, 36.3 mmol, 1 equiv.) in THF (100 mL) was added dropwise to a stirring solution of LiHMDS (77 mL, 1M in THF, 77.0 mmol, 2.1 equiv.) at −78° C. in an Ar atmosphere. The resulting dark mixture was stirred at −78° C. for 2 hours, and then freshly distilled bromoacetonitrile (13.1 g, 109.0 mmol, 3 equiv.) was added dropwise over a period of 1 hour. The reaction mixture was stirred at −78° C. for additional 2 hours and the disappearance of the starting material (6) was confirmed by TLC analysis. The reaction was quenched by addition of HCl (120 mL, 0.5 M) and H$_2$O (200 mL). The layers were separated, and the aqueous layer was further extracted with methyl tert-butyl ether (3×200 mL). The combined organic extract was washed with saturated NaHCO$_3$ (2×250 mL), brine (2×250 mL), dried over MgSO$_4$ and filtered. The solvent was evaporated under reduce pressure to give a brown oil (15.2 g). Flash chromatography over silica gel (3:1 hexanes/ethyl acetate) afforded a colorless oil (7, 6.67 g, 10.8 mmol, 58%): $^1$H NMR (CDCl$_3$) δ1.46 (s, 9 H), 2.12–2.24 (m, 2 H), 2.77–2.82 (m, 2 H), 2.85–2.91 (m, 1 H), 3.78 (s, 3 H), 3.79 (s, 3 H), 4.32–4.49 (m, 1H), 5.13 (d,J=6.0 Hz, 1 H); $^{13}$C NMR (CDC13) δ19.4, 28.6, 34.3, 38.6, 49.8, 53.1, 80.9, 117.5, 155.9, 172.4, 172.8; HRMS m/z 314.1481 (calculated for C$_{12}$H$_{22}$N$_2$O$_4$, 314.1486).

Preparation of 8 (Scheme 3)

Compound 7 (4.60 g, 14.6 mmol) was dissolved in HOAc (120 mL) and shaken with 5% Pd on C (20 g) under H$_2$ gas (50 psi) for 3 days. The mixture was filtered over Celite. The filtrate was evaporated under reduced pressure and the residue was repeatedly evaporated from methyl tert-butyl ether to yield a light pink solid (8, 8.32 g), which was used directly in the next step. $^1$H NMR (CD$_3$OD) δ1.47 (s, 9 H), 1.85–2.10 (m, 4 H), 2.60–2.62 (m, 1 H), 2.92–2.96 (m, 2 H), 3.74 (s, 3 H), 3.77 (s, 3 H), 4.22–4.26 (m, 1 H); Note: Experiments have demonstrated that less 5% Pd on C can drive the reaction to completion, i.e., 1 g of 5% Pd on C was efficient for the reduction of 2 g of 7.

Preparation of 9 (Scheme 3)

Crude 8 was dissolved in 1:1 MeOH/THF (40 mL) and Et$_3$N (7 mL) was added to the solution. The resulting mixture was stirred at 45° C. for 10 hours until the disappearance of the starting material monitored by $^1$H NMR. After stripping off the solvent on a rotovapor, methyl tert-butyl ether (200 mL) was added and a white solid precipitated out. The solid precipitate was removed by filtration. The filtrate was diluted with 200 mL of H$_2$O followed by addition of 0.5 M HCl (5 mL). The phases were split, and the aqueous phase was extracted with ethyl acetate (4–200 mL). The combined organic phases were washed with brine (2–700 mL), dried over MgSO$_4$, filtered and concentrated on a rotovapor to give a light brown oil. Flash chromatography furnished a white solid (9, 2.5 g, 8.74 mmol, 60%): $^1$H NMR (CDCl$_3$) δ1.37 (s, 9 H), 1.75–1.80 (m, 2 H), 2.04–2.09 (m, 1 H), 2.39–2.42 (m, 2 H), 3.25–3.29 (m, 2 H), 3.67 (s, 3 H), 4.23–4.26 (m, 1 H), 5.47 (d,J=8.0 Hz, 1 H), 6.29 (s, 1 H); $^{13}$C NMR (CDC13) δ28.5. 28.6, 34.5, 38.5, 40.7, 52.7, 52.8, 80.3, 156.1, 173.3, 180.0; HRMS m/z 286.1564 (calculated for C$_{13}$H$_{22}$N$_2$O$_5$, 286.1587).

Preparation of 5 from 4 (Scheme 2)

To a solution of 4 (400 g, 0.85 mol, 1 equiv.) in tetrahydrofuran (3.0 L) was added a solution of cobalt (II) chloride hexahydrate (200 g, 0.85 mol, 1 equiv.) in methanol (3.0 L). The resulting solution was cooled to 0° C. and sodium borohydride (130 g, 3.51 mol, 4.4 equiv.) was added in portions over a period of 7 hours. The reaction mixture was allowed to warm to ambient temperature and stirred for 20 hours while being monitored by TLC for the disappearance of the starting material (4). The reaction was cooled to 0° C. and quenched by addition of 1.0 M HCl (14 L) and ethyl acetate (12 L). The phases were separated and the aqueous phase was charged with 2.0 kg of sodium chloride and 4.0 L of ethyl acetate. The phases were separated, and the organic phases were combined, washed with brine (1×3.0 L), concentrated on a rotary evaporator to afford a crude material (440 g), which was used directly in the following hydrolysis reaction. To a solution of the crude material (440 g, 1 equiv.) in methanol (800 mL) was added p-toluensulfonic acid monohydrate (4.0 g, 0.015 equiv.). The reaction was stirred at ambient temperature overnight. The solvent was removed on a rotary evaporator and the residue was dissolved in ethyl acetate (2.0 L), washed with saturated sodium bicarbonate (2×100 mL). The combined aqueous phases were extracted with ethyl acetate (2×200 mL). All the organic phases were combined, concentrated on a rotary evaporator to afford 275 g of the crude product, which was charged with a solution of 2.5% methanol (20 mL) in water (780 mL) and stirred at ambient temperature overnight. The granular solid (chiral auxiliary) was removed by filtration and the filtrate was concentrated on a rotary evaporator. The residue was dissolved in ethyl acetate (1.5 L), dried over MgSO$_4$, filtered and concentrated to afford a viscous oil. The oil was further purified through a titration process using 1:1 ethyl acetate (1 L) and hexanes (1 L) to afford 5 as a white solid (104 g, 47% overall yield from 4).

Preparation of 5 from 9 (Scheme 3)

To a stirring solution of 9 (1.75 g, 6.10 mmol) in THF (40 mL) was added LiBH$_4$ (270 mg, 12.2 mmol, 2 equiv.) in several portions at 0° C. in an Argon atmosphere. The reaction mixture was stirred at 0° C. for 10 minutes, then allowed to warm to ambient temperature and stirred for additional 2 hours. The reaction was quenched by the dropwise addition of 0.5 M HCl (24 mL) with cooling in an ice bath (Note: formation of gases was observed). The solution was diluted with ethyl acetate (100 mL) and H$_2$O (50 mL). The phases were split, and the aqueous layer was extracted with ethyl acetate (6×150 mL). The combined organic phases were dried over MgSO$_4$, filtered and concentrated on rotovapor to give a light brown oil. Flash chromatography afforded a white solid (5, 1.308 g, 5.06 mmol, 83%): $^1$H NMR (CDCl$_3$) δ1.46 (s, 9 H), 1.61–1.67 (m, 1 H), 1.82–1.91 (m, 1 H), 1.94–2,00 (m, 1 H), 2.43–2.48 (m, 1 H), 2.49–2.55 (m, 1 H), 3.32–3.34 (m, 3 H), 3.58–3.66 (m, 2 H) 3.68–3.79 (m, 2 H), 5.47 (d,J=7.0 Hz, 1 H), 6.24 (s, 1 H); $^{13}$C NMR (CDCl$_3$) δ28.8, 32.9, 38.4, 40.8, 51.5, 66.3, 79.8, 157.0, 181.3; HRMS m/z 258.1652 (calculated for C$_{13}$H$_{22}$N$_2$O$_5$, 258.1650).

Preparation of 1 from 5
Procedure A (Scheme 2)

To a solution of 5 (50.0 g, 0.184 mol, 1 equiv.) methylsulfoxide (500 mL) was added triethylamine (116 mL). The resulting solution was cooled to 5° C. with an ice bath, followed by addition of sulfur trioxide-pyridine complex (132 g). The reaction was stirred at that temperature for 15 min. The cold bath was removed and the reaction was stirred for additional 1 hour. (Carboethoxymethylenetriphenyl)-phosphorane (112 g) was added in one lot and the reaction was stirred at ambient temperature for 3 hours. The reaction was quenched by addition of saturated brine (3.0 L), extracted with ethyl acetate (3×1.5 L). The combined organic phases were washed with saturated brine (3×5 L), dried over MgSO$_4$, filtered and concentrated to afford a dark red oil. The oil was purified through a chromatography, followed by a titration process using ethyl acetate (60 mL) and excess of hexanes (240 mL). 1 was obtained as a white solid (36.0 g, 60%).

Procedure B (Scheme 3)

To a solution of 5 (1.0 g, 3.87 mmol, 1 equiv.) in CH$_2$Cl$_2$ (80 mL) was added benzoic acid (1.89 g, 15.5 mmol., 4 equiv.), (carboethoxymethylenetriphenyl)phosphorane (5.39g, 15.5 mmol, 4 equiv.) and DMSO (4.8 mL). Dess-Martin periodinane (4.1 g, 9.17 mmol, 2.5 equiv.) was added in several portions to the solution, and the reaction mixture was then stirred for 5 hours at ambient temperature until the disappearance of the starting material 5. Saturated NaHCO$_3$ solution was added, and the mixture was stirred for 30 minutes. A white solid precipitated out, which was then filtered off. The organic phase of the filtrate was separated, washed with brine (250 mL), and concentrated on rotovapor to give a brown oil, which was purified by flash chromatography to produce a light brown foam (0.956 g). The foam was dissolved in ethyl acetate (3 mL). Excess hexanes (12 mL) was added gradually to the stirring solution and a white solid precipitated out. The solid was filtered and dried in vacuum oven overnight to afford 1 (0.69 g, 2.11 mmol, 55%). Chiral HPLC: 97% pure, 98% de and 100% E isomer; $^1$H NMR (CDCl$_3$) δ1.22 (t, J=7.2 Hz, 3 H), 1.38 (s, 9 H), 1.53–1.58 (m, 1 H), 1.66–1.84 (m, 1 H), 1.85–2.00 (m, 1 H), 2.30–2.50 (m, 2 H), 3.20–3.37 (m, 2H), 4.13 (q,J=7.2 Hz, 2 H), 4.20–4.35 (m, 1 H), 5.13 (d,J=7.5 Hz, 1 H), 5.68 (s, 1 H), 5.90 (dd,J=1.8, 15.6 Hz, 1 H), 6.80 (dd, J=5.1, 15.6 Hz, 1 H); HRMS m/z 326.1846 (calculated for C$_{16}$H$_{26}$N$_2$O$_6$, 326.1840).

Preparation of AG7088 from 1 and 2 (Scheme 1)

751 mg of compound 1 was dissolved in DCM (10 mL/g of 1) in a single neck round bottom flask and cover with a septum. The flask was then purged with nitrogen followed by the addition of 1.4 mL TFA via syringe while the solution was being stirred. The progress of the reaction was monitored by TLC using 5% MeOH in DCM until after about 4 hours the starting material disappeared. The solvent and excess TFA were removed under vacuum at pressure of <50 mTorr @ 45° C. The product, compound 1A, was used immediately in the step set forth below.

Compounds 1A and 2 were dissolved in DMF (7 mL/g of 2) in a single neck flask covered with a septum and fitted with a temperature probe. The flask was purged with nitrogen. The resulting solution was divided into two portions. In a first portion was added 1.6 mL n-methylmorpholine via syringe and cooled to 0° C.±5° C. In a second portion of the solution 281 mg CDMT was dissolved. This CDMT solution was then added dropwise via syringe to the first portion of the solution, maintaining the reaction temperature of 0° C.±5° C. The resulting reaction mixture was then allowed to warm to room temperature. The reaction was monitored for about 1 hour by TLC (7:3:1 hexanes:EtOAc:IPA) until the compound 2 disappeared. Once the reaction was complete the product AG7088 was precipitated out of solution by the slow addition of water to reaction mixture. The resulting slurry was filtered to obtain a yield of >85% white granular crystals of compound AG7088 having a purity of >97%. The product may then be recrystallized by dissolving it in hot MeOH:EtOAc 1:1 followed by slow addition of hexanes (2 vols.)

It is to be understood that the foregoing description is exemplary and explanatory in nature, and is intended to illustrate the invention and its preferred embodiments. Through routine experimentation, the artisan will recognize apparent modifications and variations that may be made without departing from the spirit of the invention. Thus, the invention is intended to be defined not by the above description, but by the following claims and their equivalents.

What is claimed is:

1. A process useful in synthesizing antipicornaviral compounds, comprising:

(a) performing cyanomethylation of a compound of formula V using bis(trimethysily)amide and bromoacetonitrile to yield a compound of formula VI;

(V)

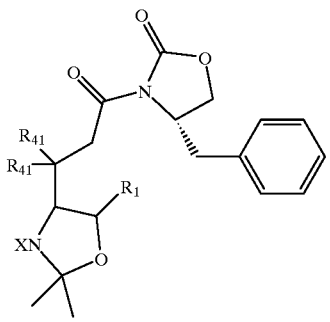

(VI)

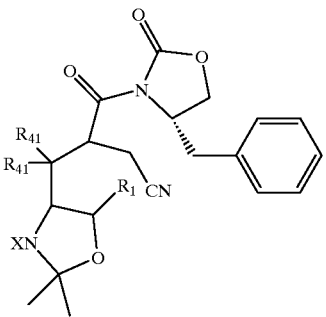

(b) performing reduction, then cyclization, and then deprotection of the compound of formula VI to yield a compound of formula VII; and (VII)

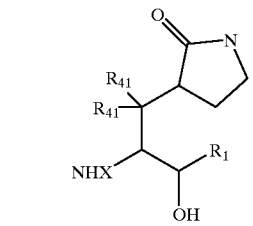

(c) performing oxidation and olefination of the compound of formula VII by reacting the compound of formula VII with a SO$_3$-pyridine complex to yield a (VIII)

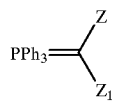

(IV)

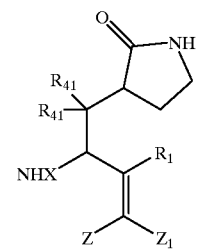

reaction mixture and reacting the reaction mixture with a compound for formula VIII to form a compound of formula IV:

(d) deprotecting the compound of formula IV to yield a compound of formula IVA:

(IVA)

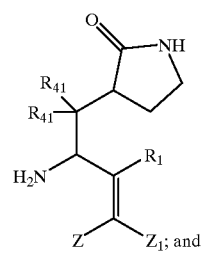

(e) subjecting a compound of formula II and the compound of formula IVA to an amide-forming reaction to yield a compound of formula IA:

(II)

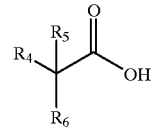

(IA)

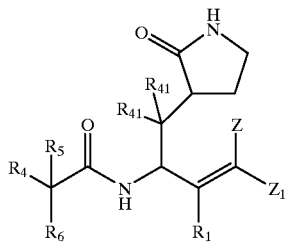

wherein
each $R_{41}$ is independently H or lower alkyl, $R_4$ is

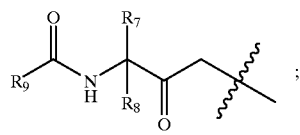

R$_5$ and R$_6$ are each independently H, F, an alkyl group, a cycloalkyl group, a heterocycloalkyl group, an aryl group, or a heteroaryl group; and Z and Z$_1$ are each independently H, F, an alkyl group, a cycloalkyl group, a heterocycloalkyl group, an aryl group, a heteroaryl group, —C(O)R$_{21}$, —CO$_2$R$_{21}$, CN, —C(O)NR$_{21}$R$_{22}$, —C(O)NR$_{21}$OR$_{22}$, —C(S) R$_{21}$, —C(S)NR$_{21}$R$_{22}$, —NO$_2$, —SOR$_{21}$, —SO$_2$R$_{21}$, wherein R$_1$ is H, F, an alkyl group, OH, SH, or an O-alkyl group;

wherein each R$_{41}$ is independently H or lower alkyl;

wherein X is any suitable protecting group for nitrogen and wherein Z and Z$_1$ are each independently H, F, an alkyl group, a cycloalkyl group, a heterocycloalkyl group, an aryl group, a heteroaryl group, —C(O)R$_{21}$, —CO$_2$R$_{21}$, CN, —C(O)NR$_{21}$R$_{22}$, —C(O)NR$_{21}$OR$_{22}$, —C(S)R$_{21}$, —C(S)NR$_{21}$R$_{22}$, —NO$_2$, —SOR$_{21}$, —SO$_2$R$_{21}$, —SO$_2$NR$_{21}$R$_{22}$, —SO(NR$_{21}$)(OR$_{22}$), —SONR$_{21}$, —SO$_3$R$_{21}$, —PO (OR$_{21}$)$_2$, —PO(R$_{21}$)(R$_{22}$), —PO(NR$_{21}$R$_{22}$)(OR$_{23}$), —PO(NR$_{21}$R$_{22}$)(NR$_{23}$R$_{24}$), —C(O)NR$_{21}$NR$_{22}$R$_{23}$, or —C(S)NR$_{21}$NR$_{22}$R$_{23}$, where R$_{21}$, R$_{22}$, R$_{23}$, and R$_{24}$ are each independently H, an alkyl group, a cycloalkyl group, a heterocycloalkyl group, an aryl group, a heteroaryl group, an acyl group, or a thioacyl group, or where any of two of R$_{21}$, R$_{22}$, R$_{23}$, and R$_{24}$, together with the atom(s) to which they are bonded, form a heterocycloalkyl group, provided that Z and Z$_1$ are not both H;

or Z$_1$ and R$_1$, together with the atoms to which they are bonded, form a cycloalkyl or heterocycloalkyl group, where Z$_1$ and R$_1$ are as defined above except for moieties that cannot form the cycloalkyl or heterocycloalkyl group;

or Z and Z$_1$, together with the atoms to which they are bonded, form a cycloalkyl or heterocycloalkyl group, where Z and Z$_1$ are as defined above except for moieties that cannot form the cycloalkyl or heterocycloalkyl group.

2. The process of claim 1, wherein the compound of formula V is prepared from N-Boc L glutanic acid γ-benzyl ester.

3. The process of claim 1, wherein X is a Boc group.
4. The process of claim 1, wherein R$_{41}$ is H.
5. The process of claim 1, wherein Z is H.
6. The process of claim 1, wherein Z$_1$ is —COOEt.
7. A process useful in synthesizing antipicornaviral compounds according to claim 1, further comprising the steps of: —SO$_2$NR$_{21}$R$_{22}$, —SO(NR$_{21}$)(OR$_{22}$), —SONR$_{21}$, —SO$_3$R$_{21}$, —PO(OR$_{21}$)$_2$, —PO(R$_{21}$)(R$_{22}$), —PO (NR$_{21}$R$_{22}$)(OR$_{23}$), —PO(NR$_{21}$R$_{22}$)(NR$_{23}$R$_{24}$), —C(O) NR$_{21}$ NR$_{22}$R$_{23}$, or —C(S)NR$_{21}$NR$_{22}$R$_{23}$, where R$_{21}$, R$_{22}$, R$_{23}$, and R$_{24}$ are each independently H, an alkyl group, a cycloalkyl group, a heterocycloalkyl group, an aryl group, a heteroaryl group, an acyl group, or a thioacyl group, or where any of two of R$_{21}$, R$_{22}$, R$_{23}$, and R$_{24}$, together with the atom(s) to which they are bonded, form a heterocycloalkyl group, provided that Z and Z$_1$ are not both H;

or Z$_1$ and R$_1$, together with the atoms to which they are bonded, form a cycloalkyl or heterocycloalkyl group, where Z$_1$ and R$_1$ are as defined above except for moieties that cannot form the cycloalkyl or heterocycloalkyl group;

or Z and Z$_1$, together with the atoms to which they are bonded, form a cycloalkyl or heterocycloalkyl group, where Z and Z$_1$ are as defined above except for moieties that cannot form the cycloalkyl or heterocycloalkyl group.

8. The process of claim 7, wherein X is a Boc group.
9. The process of claim 7, wherein compound IV is

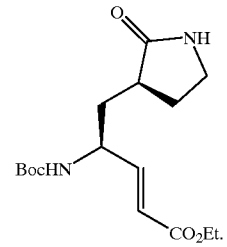

10. The process of claim 7, wherein the compound of formula II is

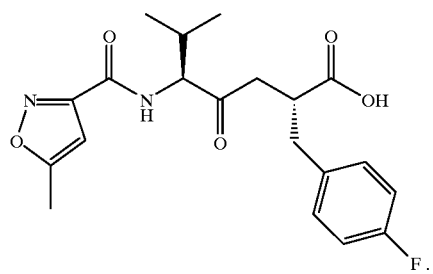

11. The process of claim 7, wherein the compound of formula IVA is

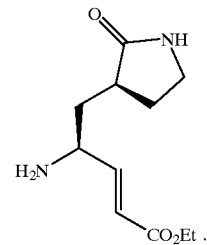

12. The process according to claim 7, wherein the compound of formula IA is

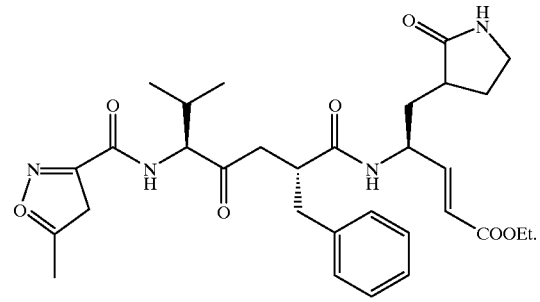

13. A process useful in synthesizing antipicornaviral compounds, comprising:

(a) performing dianionic alkylation of a compound of formula IX using bromoacetonitrile to prepare a compound of formula X;

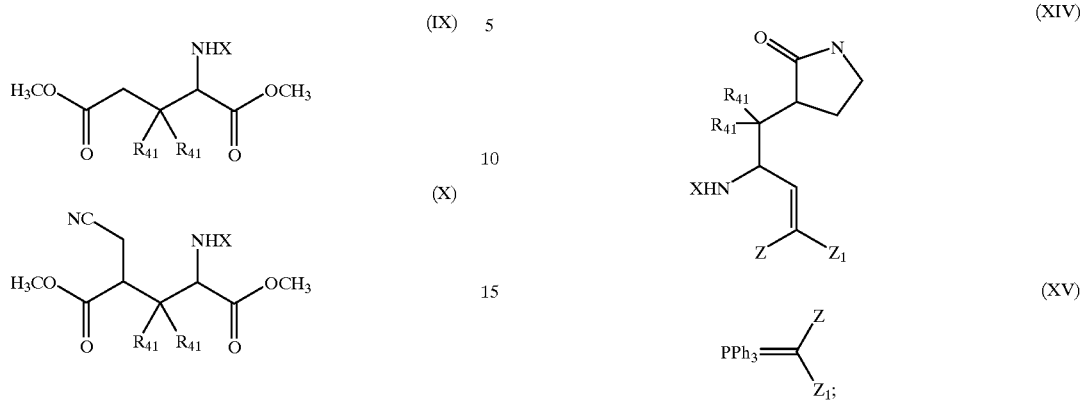

(b) performing hydrogenation of the compound of formula X to yield an amine of formula XI;

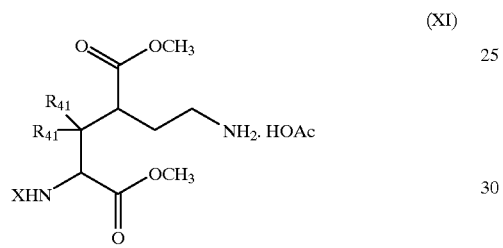

(c) reacting the compound of formula XI with Et₃N to yield a lactam ester of formula XII;

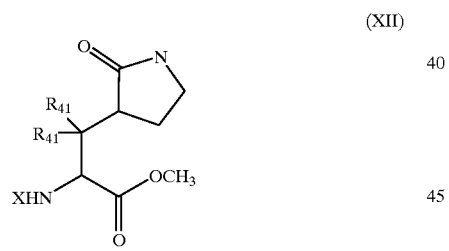

(d) performing reduction of the lactam ester of formula XII to yield a compound of formula XIII:

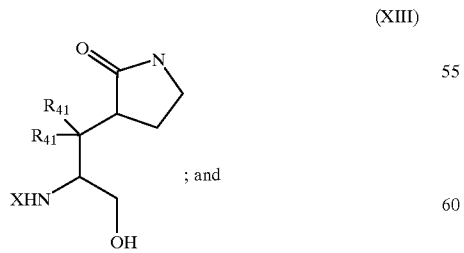

; and (e) performing oxidation and olefination of the compound of formula XIII to yield a compound of formula XIV by reacting it with a compound of formula XV:

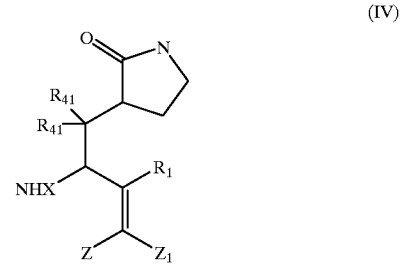

wherein
each $R_{41}$ is independently H or lower alkyl;
Z and $Z_1$ are each independently H, F, an alkyl group, a cycloalkyl group, a heterocycloalkyl group, an aryl group, a heteroaryl group, $-C(O)R_{21}$, $-CO_2R_{21}$, CN, $-C(O)NR_{21}R_{22}$, $-C(O)NR_{21}OR_{22}$, $-C(S)R_{21}$, $-C(S)NR_{21}R_{22}$, $-NO_2$, $-SOR_{21}$, $-SO_2R_{21}$, $-SO_2NR_{21}R_{22}$, $-SO(NR_{21})(OR_{22})$, $-SONR_{21}$, $-SO_3R_{21}$, $-PO(OR_{21})_2$, $-PO(R_{21})(R_{22})$, $-PO(NR_{21}R_{22})(OR_{23})$, $-PO(NR_{21}R_{22})(NR_{23}R_{24})$, $-C(O)NR_{21}NR_{22}R_{23}$, or $-C(S)NR_{21}NR_{22}R_{23}$, where $R_{21}$, $R_{22}$, $R_{23}$, and $R_{24}$ are each independently H, an alkyl group, a cycloalkyl group, a heterocycloalkyl group, an aryl group, a heteroaryl group, an acyl group, or a thioacyl group, or where any of two of $R_{21}$, $R_{22}$, $R_{23}$, and $R_{24}$, together with the atom(s) to which they are bonded, form a heterocycloalkyl group, provided that Z and $Z_1$ are not both H;
or Z and $Z_1$, together with the atoms to which they are bonded, form a cycloalkyl or heterocycloalkyl group, where Z and $Z_1$ are as defined above except for moieties that cannot form the cycloalkyl or heterocycloalkyl group; and
X is any suitable protecting group for nitrogen.

14. The process useful in synthesizing antipicornaviral compounds according to claim 13, further comprising:
preparing a compound of formula IV by converting the compound of formula XIV to yield the compound of formula IV:

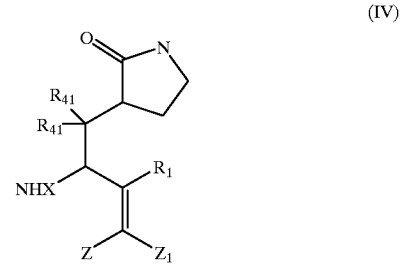

wherein $R_1$ is H, F, an alkyl group, OH, SH, or an O-alkyl group.

15. The process useful in synthesizing antipicornaviral compounds according to claim 14, further comprising:
Step A: deprotecting the compound of formula IV to yield a compound of formula IVA:

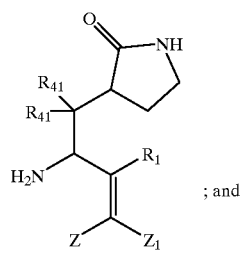
(IVA)

Step B: subjecting a compound of formula II and the compound of formula IVA to an amide-forming reaction to yield a compound of formula IA:

(II)

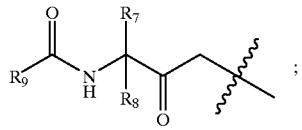

(IA)

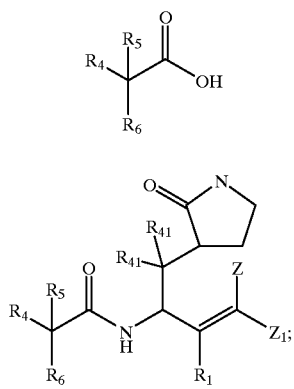

wherein
each $R_{41}$ is independently H or lower alkyl, $R_4$ is (structure shown)

$R_5$ and $R_6$ are each independently H, F, an alkyl group, a cycloalkyl group, a heterocycloalkyl group, an aryl group, or a heteroaryl group;

Z and $Z_1$ are each independently H, F, an alkyl group, a cycloalkyl group, a heterocycloalkyl group, an aryl group, a heteroaryl group, —C(O)$R_{21}$, —CO$_2R_{21}$), CN, —C(O)NR$_{21}$R$_{22}$, —C(O)NR$_{21}$OR$_{22}$, —C(S) R$_{21}$, —C(S)NR$_{21}$R$_{22}$, —NO$_2$, —SOR$_{21}$, —SO$_2$R$_{21}$, —SO$_2$NR$_{21}$R$_{22}$, —SO(NR$_{21}$)(OR$_{22}$), —SONR$_{21}$, —SO$_3$R$_{21}$, —PO(OR$_{21}$)$_2$, —PO(R$_{21}$)(R$_{22}$), —PO (NR$_{21}$R$_{22}$)(OR$_{23}$), —PO(NR$_{21}$R$_{22}$)(NR$_{23}$R$_{22}$), —C(O)NR$_{21}$NR$_{22}$R$_{23}$, or —C(S)NR$_{21}$NR$_{22}$R$_{23}$, where $R_{21}$, $R_{22}$, $R_{23}$, and $R_{24}$ are each independently H, an alkyl group, a cycloalkyl group, a heterocycloalkyl group, an aryl group, a heteroaryl group, an acyl group, or a thioacyl group, or where any of two of $R_{21}$, $R_{22}$, $R_{23}$, and $R_{24}$, together with the atom(s) to which they are bonded, form a heterocycloalkyl group, provided that Z and $Z_1$ are not both H;

or $Z_1$ and $R_1$, together with the atoms to which they are bonded, form a cycloalkyl or heterocycloalkyl group, where $Z_1$ and $R_1$ are as defined above except for moieties that cannot form the cycloalkyl or heterocycloalkyl group;

or Z and $Z_1$, together with the atoms to which they are bonded, form a cycloalkyl or heterocycloalkyl group, where Z and $Z_1$ are as defined above except for moieties that cannot form the cycloalkyl or heterocycloalkyl group.

16. The process of claim 13, wherein X is a Boc group.
17. The process of claim 13, wherein $R_{41}$ is H.
18. The process of claim 13, wherein Z is H.
19. The process of claim 13, wherein $Z_1$ is —COOEt.
20. The process of claim 14, wherein $R_1$ is H.
21. A process useful for the synthesis of a compound of formula IA', and acid addition salts thereof:

(IA')

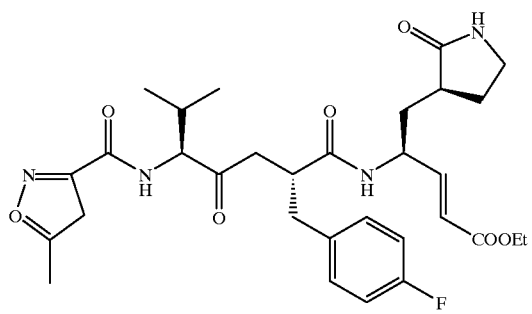

comprising the steps of:
Step A: preparing a compound of formula IV':

(IV')

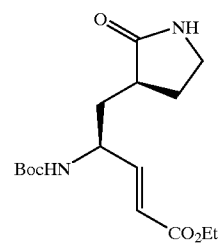

comprising:
performing cyanomethylation of a compound of formula V' using bis(trimethysily)amide and bromoacetonitrile to yield a compound of formula VI';

(V')

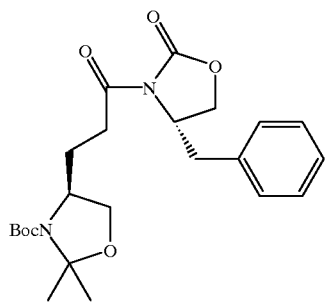

performing reduction, then cyclization, and then deprotection of the compound of formula VI' to yield a compound of formula VII'; and (VI')

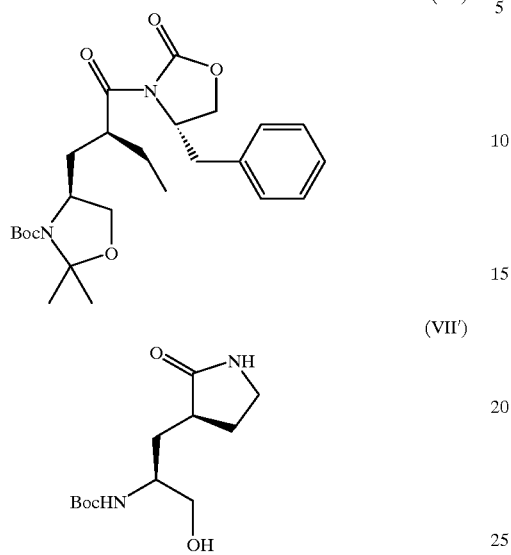

performing oxidation and olefination of the compound of formula VII by reacting the compound with a SO₃-pyridine complex before the resulting reaction mixture is reacted with Ph₃P=CHCO₂Et;

Step B: deprotecting the compound of formula IV to yield a compound of formula IVA':

(IVA')

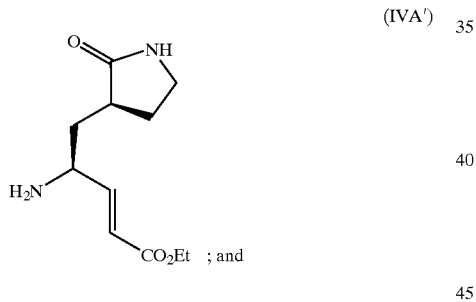

; and

Step C: subjecting a compound of formula II' and the compound of formula formula IVA' to an amide-forming reaction;

(II')

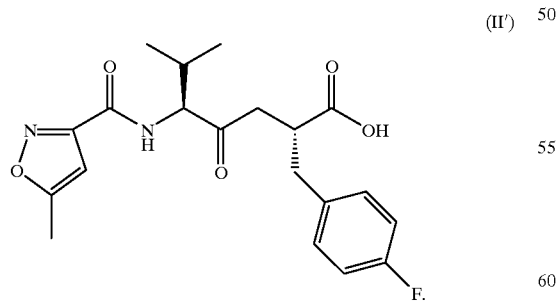

22. The process of claim 21, wherein the compound of formula V is prepared from N-Boc L glutanic acid γ-benzyl ester.

23. A process useful in synthesizing antipicornaviral compounds, comprising:

(a) performing dianionic alkylation of a compound of formula IX' using bromoacetonitrile to prepare a compound of formula X';

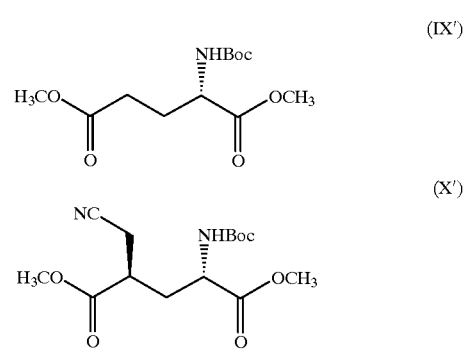

(b) performing hydrogenation of the compound of formula X' to yield an amine of formula XI';

(XI')

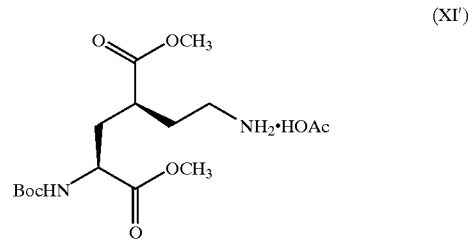

(c) reacting the compound of formula XI' with Et₃N to yield a lactam ester of formula XII';

(XII')

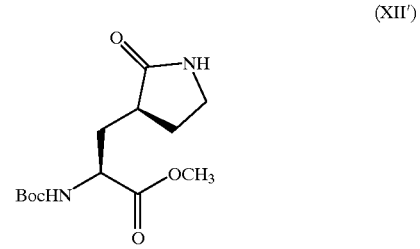

(d) performing reduction of the lactam ester of formula XII' to yield a compound of formula XIII':

(XIII')

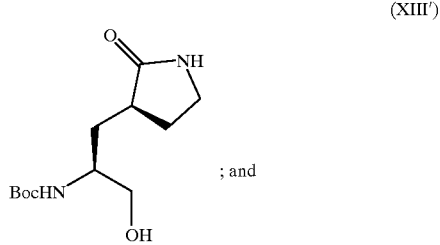

; and (e) performing oxidation and olefination of the compound of formula XIII' to yield a compound of formula XIV' by reacting it with Ph₃P=CHCO₂Et;

(XIV')

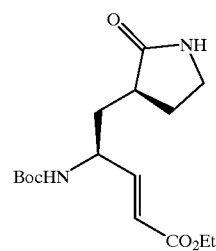

24. The process useful in synthesizing antipicornaviral compounds according to claim 23, further comprising:

converting the compound of formula XIV' to the compound of formula IV';

(IV')

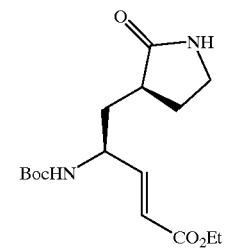

25. The process useful in synthesizing antipicornaviral compounds according to claim 24, further comprising:

Step A: deprotecting the compound of formula IV' to yield a compound of formula IVA':

(IVA')

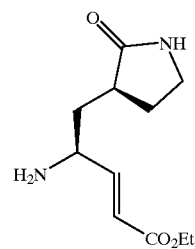

and

Step C: subjecting a compound of formula II' and the compound of formula IVA' to an amide-forming reaction;

(II')

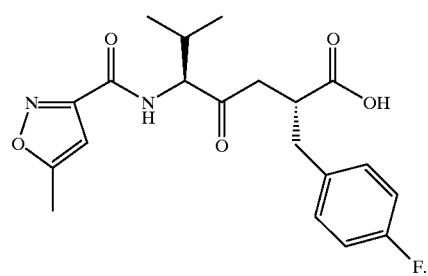

* * * * *